(12) United States Patent
Bathe et al.

(10) Patent No.: US 8,554,489 B2
(45) Date of Patent: Oct. 8, 2013

(54) METHOD AND APPARATUS FOR CONTROLLING PROPERTIES OF NUCLEIC ACID NANOSTRUCTURES

(75) Inventors: Mark Bathe, Cambridge, MA (US); Do-Nyun Kim, Cambridge, MA (US); Hendrik Dietz, Munich (DE)

(73) Assignee: Massachusetts Institute of Technology, Cambridge, MA (US)

( * ) Notice: Subject to any disclaimer, the term of this patent is extended or adjusted under 35 U.S.C. 154(b) by 168 days.

(21) Appl. No.: 12/976,737

(22) Filed: Dec. 22, 2010

(65) Prior Publication Data

US 2012/0166152 A1    Jun. 28, 2012

(51) Int. Cl.
*G01N 33/50* (2006.01)

(52) U.S. Cl.
USPC .......................................................... 702/19

(58) Field of Classification Search
None
See application file for complete search history.

(56) References Cited

U.S. PATENT DOCUMENTS

| | | | |
|---|---|---|---|
| 7,842,793 B2 * | 11/2010 | Rothemund | 536/23.1 |
| 2007/0117109 A1 | 5/2007 | Rothemund | |
| 2010/0069621 A1 | 3/2010 | Maune et al. | |
| 2010/0216978 A1 | 8/2010 | Shih | |

OTHER PUBLICATIONS

Sadhasivam et al. (DNA self-assembly: prospectus and its future, Jan. 2010, 45 pp. 2543-2552).*
Mastrangeli et al. (Self-assembly from milli- to nanoscales methods and applications, Journal of Micromechanical Microengineering, 2009, 19, pp. 1-37).*
Yonggang et al. (Multilayer DNA Origami Packed on a Square Lattice, Journal of American Chemical Society, 2009, 131, pp. 15903-15908).*
Douglas,Shawn "caDNAno Intro", Dec. 1, 2010,Internet http://cadnano.org/intro.html, Cambridge, MA.
Rothemund, Paul W. K. "Folding DNA to create nanoscale shapes and patterns," Nature,vol. 440 (16) Mar. 2006, pp. 297-302, doi:10.1038/nature04586, London, UK.
Le, John D.; Pinto, Yariv; Seeman, Nadrian C.; Musier-Forsyth, Karin; Taton, T. Andrew; and Kiehl, Richard A. "DNA-Templated Self-Assembly of Metallic Nanocomponent Arrays on a Surface," Nano Lett., vol. 4 (12), pp. 2343-2347, 2343-2347• DOI: 10.1021/nl048635+, Oct. 29, 2004, American Chemical Society, Washington, DC.
Kuzyk, Anton; Yurke, Bernard; Toppari, J. Jussi; Linko Veikko; and Torma, Paivi, Dielectrophoretic Trapping of DNA Origami** Small vol. 4, No. 4, 447-450, 2008, Wiley, Weinheim, Germany.
Ke, Yonggang; Sharma, Jaswinder; Liu, Minghui; Jahn, Kasper, Liu, Yan; and Yan, Hao, "Scaffolded DNA Origami of a DNA Tetrahedron Molecular Container," Nano Lett., vol. 9 (6), pp. 2445-2447, DOI: 10.1021/nl901165f May 6, 2009, American Chemical Society, Washington, DC.

* cited by examiner

*Primary Examiner* — Jason Sims
(74) *Attorney, Agent, or Firm* — Evans & Molinelli PLLC; Eugene J. Molinelli

(57) ABSTRACT

Techniques for controlling properties of nucleic acid nanostructures include receiving data that indicates a sequence of nucleotides on at least a first strand of a nucleic acid. Values are determined for at least one physical property for each portion of the at least first strand. Based at least in part on a numerical model and the physical properties for each portion, a value is determined of at least one derived property of a nanostructure that comprises the at least first strand of nucleic acid. In some embodiments, information gained from the numerical model is used iteratively in order to optimize or improve one or more of the properties of the target DNA origami structure.

18 Claims, 24 Drawing Sheets

NANOSTRUCTURE 122

NANOSTRUCTURE 124

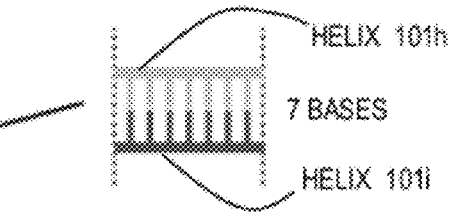
 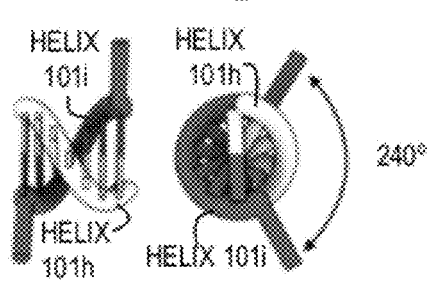
FIG. 1J  FIG. 1K

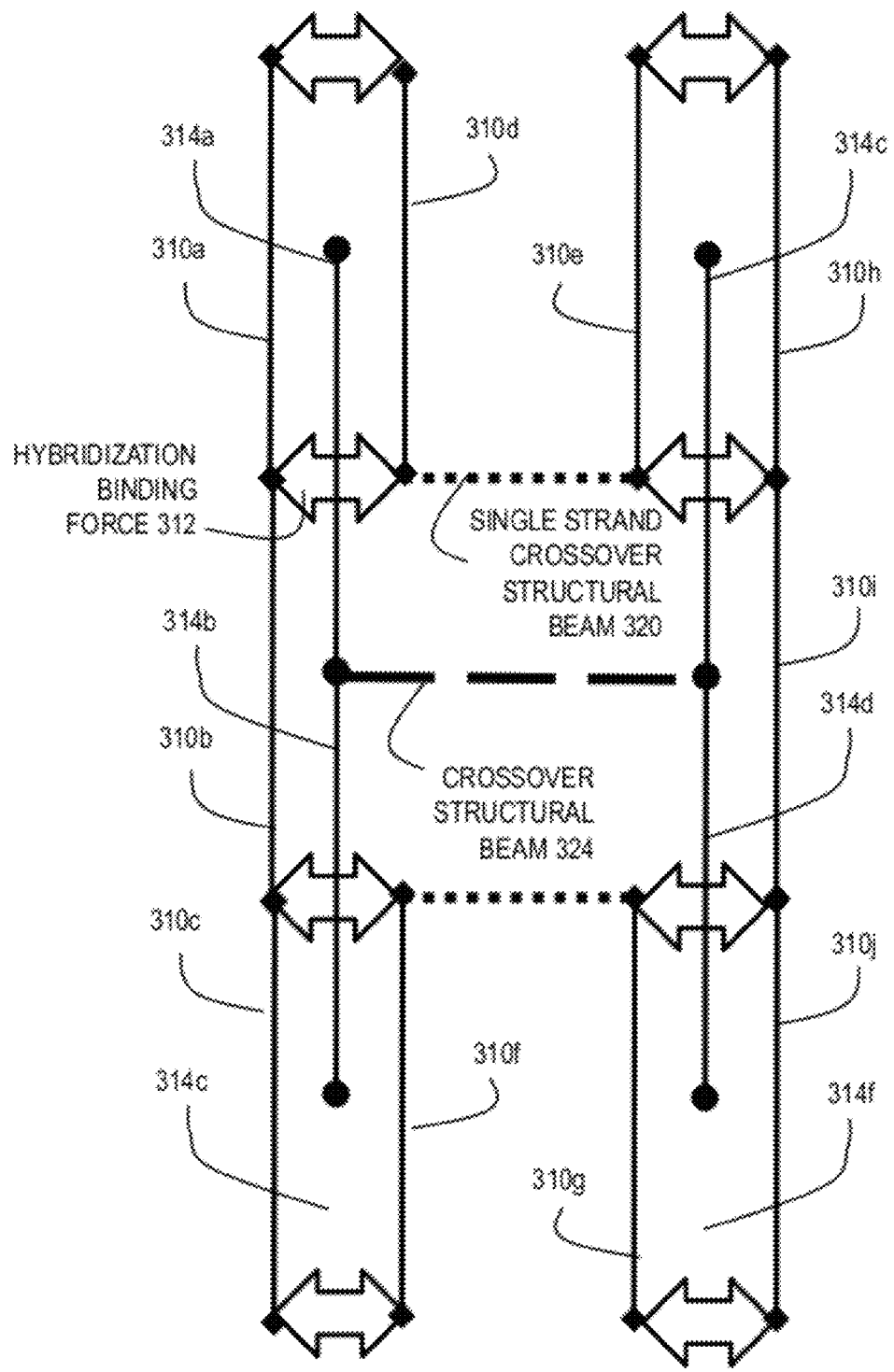

FIG. 4A
INITIAL CONFIGURATION 410
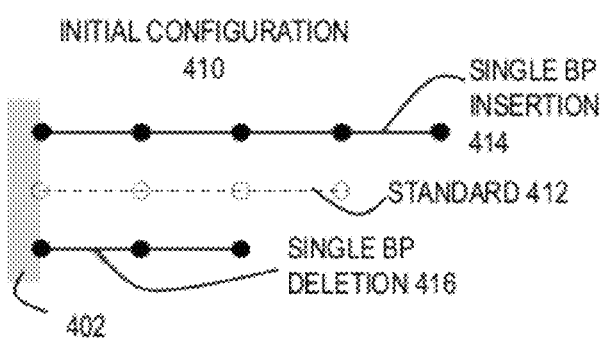
SINGLE BP INSERTION 414
STANDARD 412
SINGLE BP DELETION 416
FIG. 4B
REFERENCE (STRAINED) CONFIGURATION 420
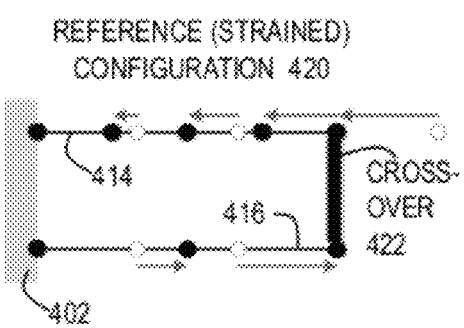
CROSS-OVER 422
FINAL (RELAXED) CONFIGURATION (ONE STEP) 430
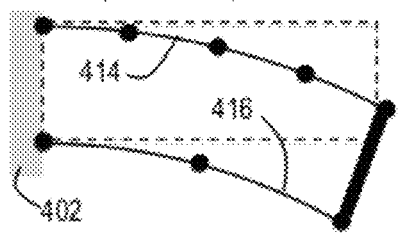
LINEAR ANALYSIS
FIG. 4C
FINAL (RELAXED) CONFIGURATION (INCREMENTAL STEPS) 440
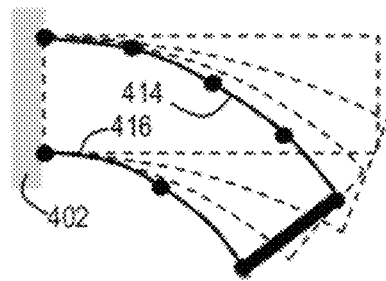
NON-LINEAR ANALYSIS
FIG. 4D

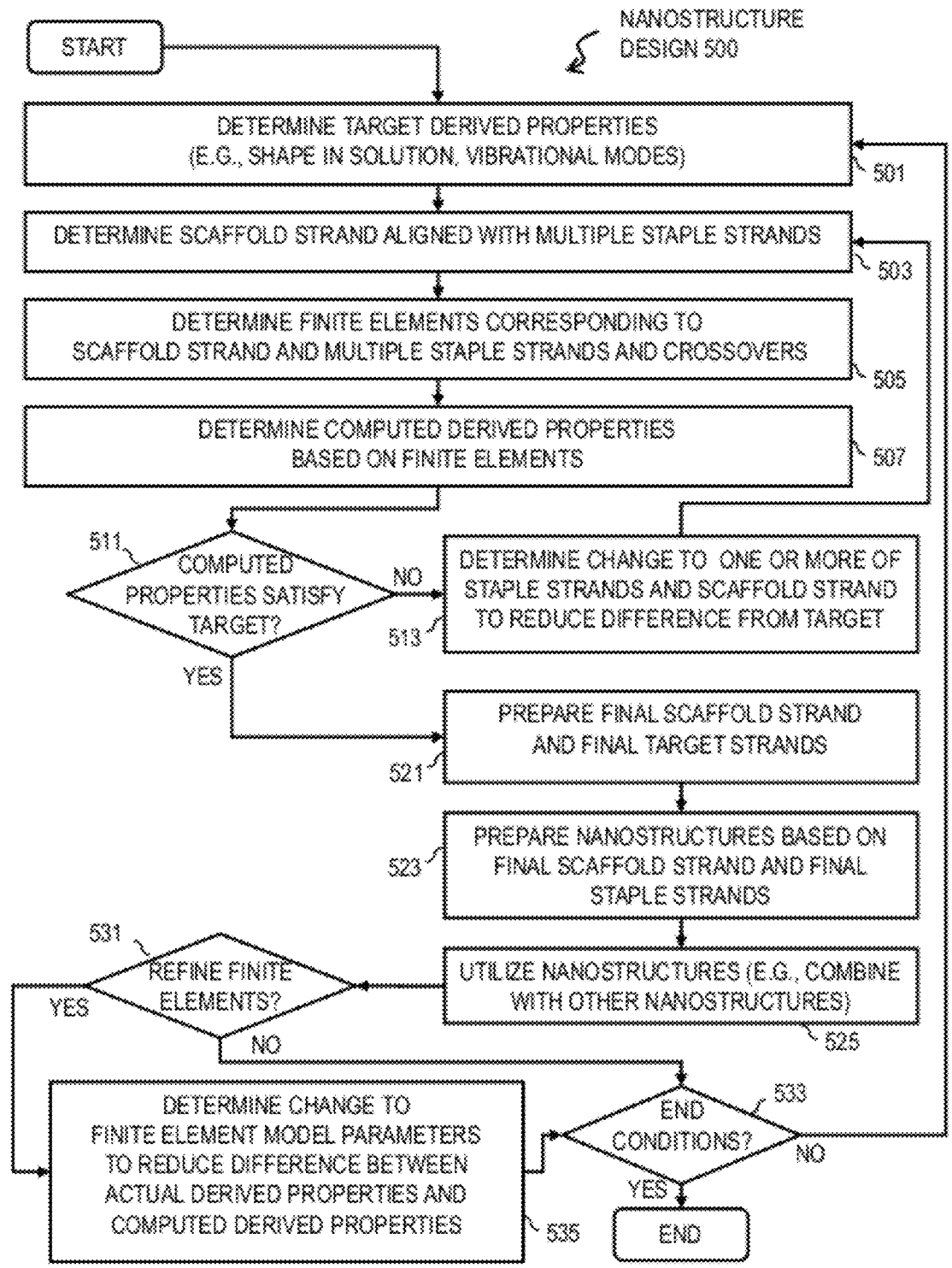

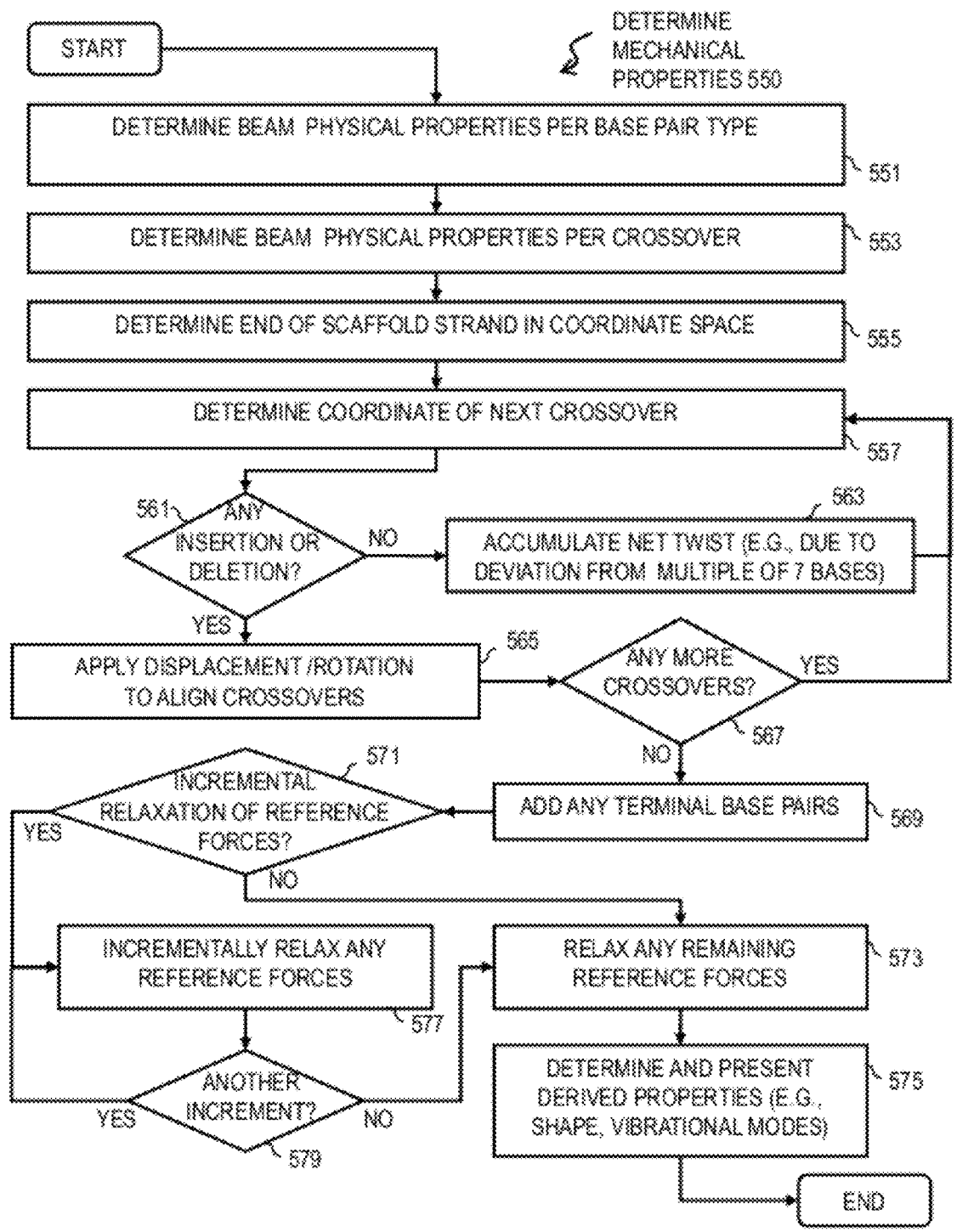

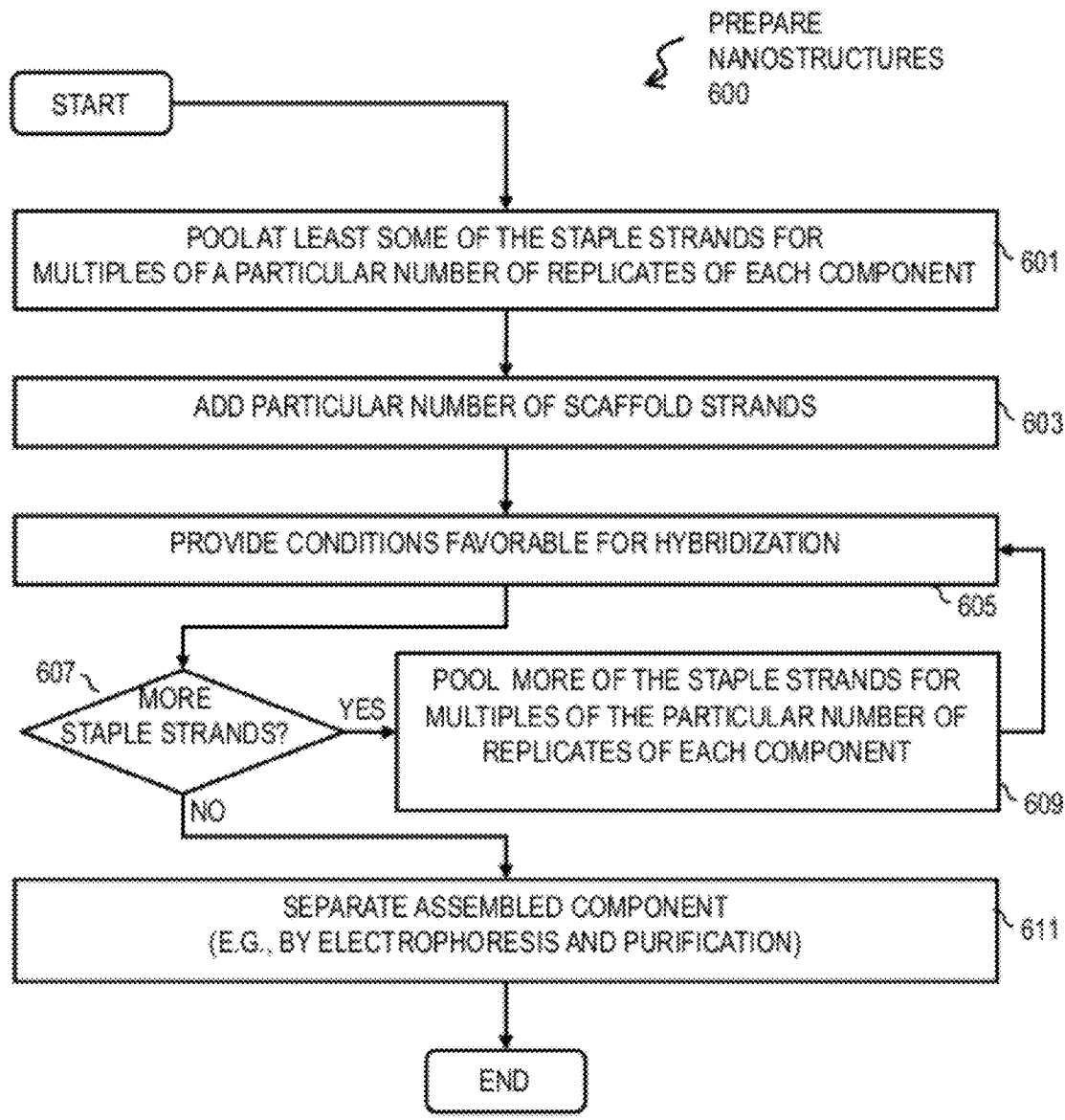

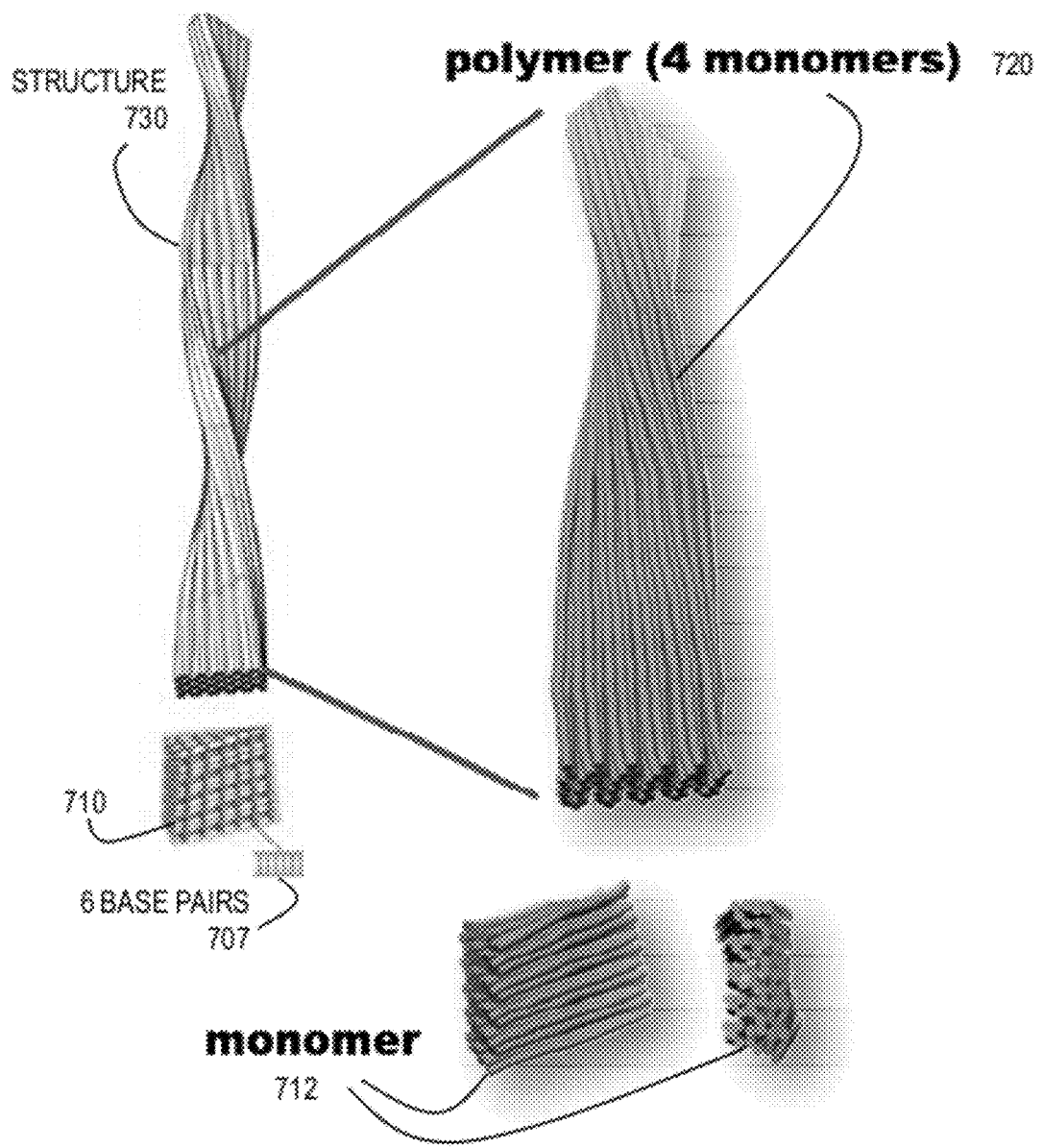

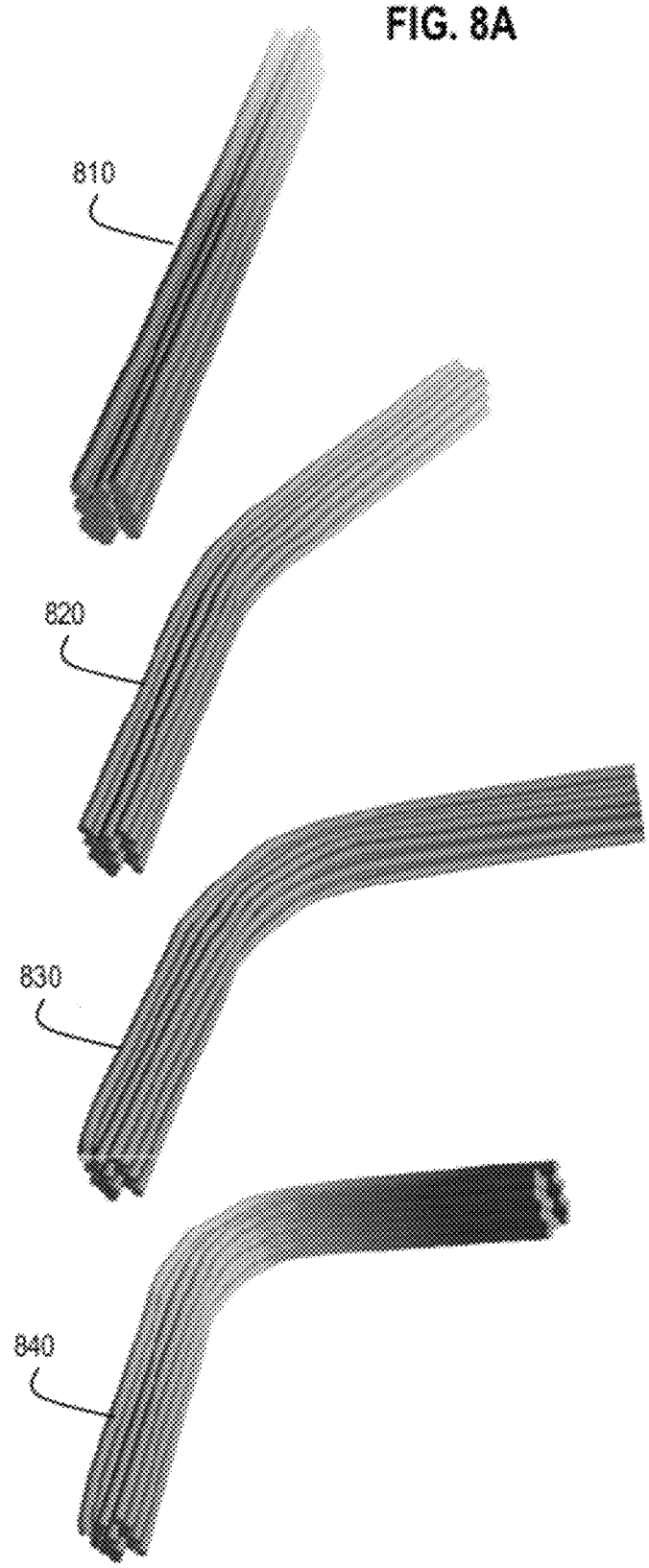

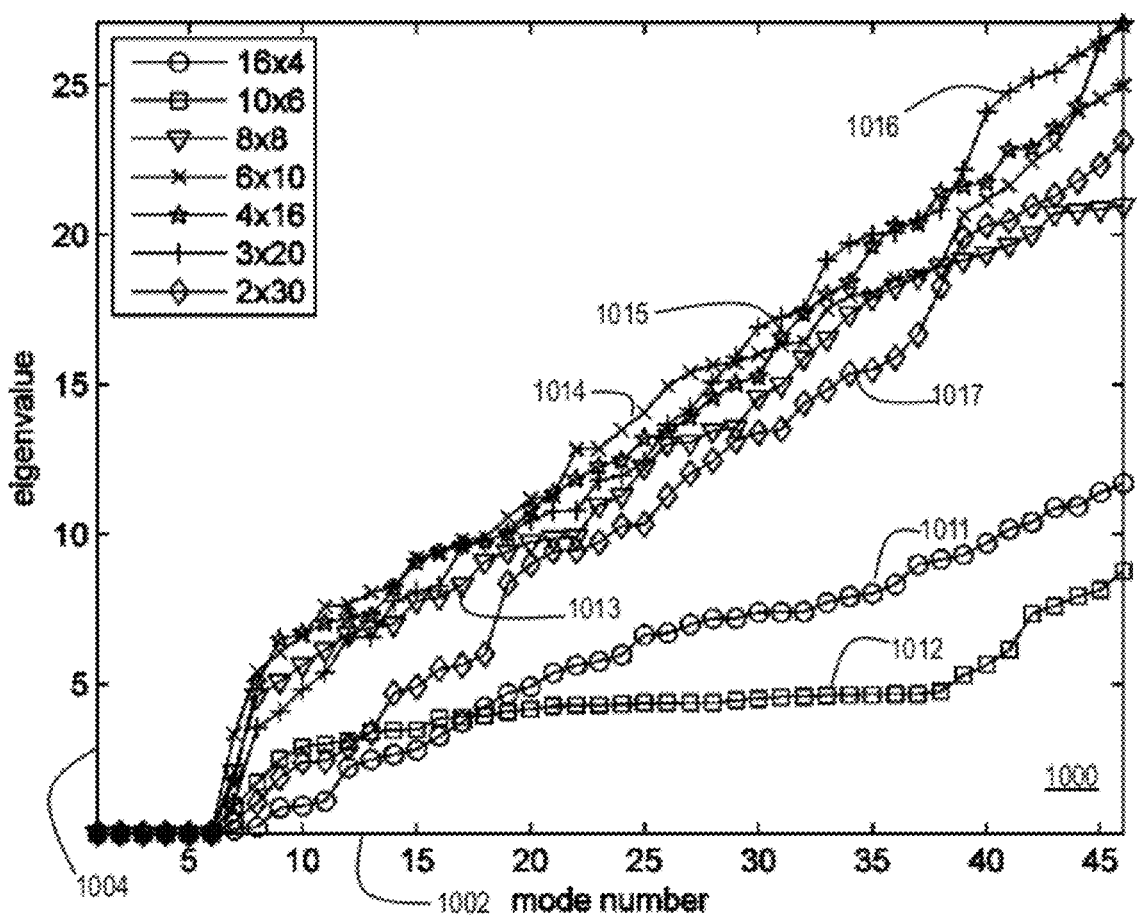

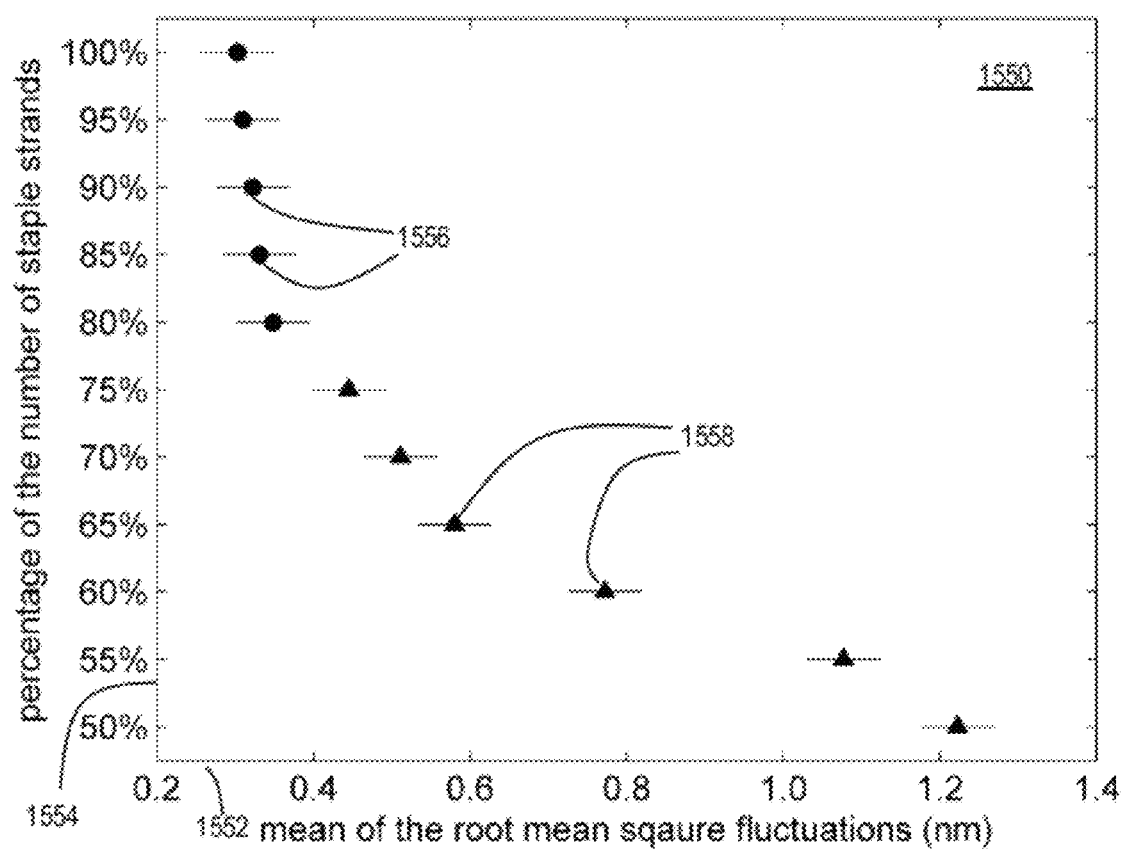

METHOD AND APPARATUS FOR CONTROLLING PROPERTIES OF NUCLEIC ACID NANOSTRUCTURES

BACKGROUND OF THE INVENTION

Molecular self-assembly with scaffolded deoxyribonucleic acid (DNA) origami enables arranging many thousand nucleotides with subnanometer precision at specified locations in space to yield custom-shaped objects with dimensions on the scale of 1 to 1000 nanometers (1 nanometer, nm, $=10^{-9}$ meters). [See Rothemund, P W K. "Folding DNA to create nanoscale shapes and patterns.", Nature, 440, 297-302, (2006); Lulu, Q., Ying, W., Zhao, Z., Jian, Z., Dun, P., Yi, Z., Qiang, L., Chunhai, F., Jun, H., Lin, H. "Analogic China map constructed by DNA", Chinese Sci Bull, 51, 2973-2976, (2006); Douglas, S M., Chou, J J., Shih, W M. "DNA-nanotube-induced alignment of membrane proteins for NMR structure determination", Proc Natl Acad Sci U.S.A., 104, 6644-6648, (2007); Andersen, E S., Dong, M., Nielsen, M M., Jahn, K., Lind-Thomsen, A., Mamdouh, W., Gothelf, K V., Besenbacher, F., Kjems, J. "DNA origami design of dolphin-shaped structures with flexible tails", ACS Nano, 2, 1213-1218, (2008); Ke Y., Sharma, J., Liu, M., Jahn, K., Liu, Y., Yan, H. "Scaffolded DNA origami of a DNA tetrahedron molecular container", Nano Lett, 9, 2445-2447, (2009); Andersen, E S., Dong, M., Nielsen, M M., Jahn, K. Subramani, R. Mamdouh, W., Golas, M M., Sander, B., Stark, H., Oliveira, C L P., Pedersen, J S., Birkedal, V., Besenbacher, F., Gothelf, K V., Kjems, J. "Self-assembly of a nanoscale DNA box with a controllable lid", Nature, 459, 73-76, (2009); Douglas, S M., Dietz, H., Liedl, T., Högberg, B., Graf, F., Shih, W M. "Self-assembly of DNA into nanoscale three-dimensional shapes.", Nature, 459, 414-418, (2009); Dietz, H., Douglas, S M., Shih, W M. "Folding DNA into twisted and curved nanoscale shapes.", Science, 325, 725-730, (2009); Douglas, S M., Marblestone, A H., Teerapittayanon, S., Vazquez, A., Church, G M., Shih, W M. "Rapid prototyping of 3D DNA-origami shapes with caDNAno", Nucleic Acids Res, 37, 5001-5006, (2009) Ke, Y., Douglas, S M., Liu, M., Sharma, J., Cheng, A., Leung, A., Liu, Y., Shih, W M., Yan, H. "Multi-layer DNA origami packed on a square lattice", J Am Chem Soc, 131, 15903-15908, (2009); Pound, E., Ashton, J R., Becerril, H A., Woolley, A T. "Polymerase chain reaction based scaffold preparation for the production of thin, branched DNA origami nanostructures of arbitrary sizes.", Nano Lett, 9, 4302-4305, (2009); Endo, M., Hidaka, K., Kato, T., Namba, K., Sugiyama, H. "DNA prism structures constructed by folding of multiple rectangular arms", J Am Chem Soc, 131, 15570-15571, (2009); Kuzuya, A., Komiyama, M. "Design and construction of a box-shaped 3D-DNA origami.", Chem Commun (Camb), 4182-4184, (2009); Liedl, T., Högberg, B., Tytell, J., Ingber, D E., Shih, W M. "Self-assembly of three-dimensional prestressed tensegrity structures from DNA", Nat Nanotechnol, 5, 520-524, (2010); for which the entire contents of each are hereby incorporated as if fully set forth herein, except as the terminology is inconsistent with the terminology used elsewhere herein].

DNA origami entails folding a single-stranded 'scaffold' DNA molecule up to several thousand bases long into custom-shaped single-layer or multi-layer bundles of B-form DNA double helices with the help of a set of short (<60 bases) single-stranded 'staple' oligonucleotides that are currently derived from chemical synthesis. DNA origami objects can be designed in a few hours with the help of software developed specifically for this purpose, and the manual labor required for setting up assembly reactions and purification is limited to handling a multi-channel pipette and running agarose gels. A rich diversity of shapes has been built so far with scaffolded DNA origami. A comprehensive review has recently been published in Shih, W M., Lin, C. "Knitting complex weaves with DNA origami", Curr Opin Struct Biol, 20, 276-282, (2010) the entire contents of which are hereby incorporated as if fully set forth herein, except as the terminology is inconsistent with the terminology used elsewhere herein.

Scaffolded DNA origami enables the programmable synthesis of complex nanoscale structures with a broad range of potential scientific and industrial applications. However, the rational design of DNA origami structures to target specifications is currently limited by a lack of quantitative tools for predicting the solution shape and mechanical integrity of designed structures, and using these predictive capabilities for unsupervised, automated design.

SUMMARY OF THE INVENTION

Thus there is a need for quantitative tools for predicting the solution shape and mechanical integrity of designed nucleic acid nanostructures. Techniques are provided for controlling derived properties of nucleic acid nanostructures based on physical properties of portions of the nucleic acid, including determining the derived properties of the nanostructures that result from scaffolded DNA origami. As used herein derived properties include elastic response properties (also called stiffness), internal strain energy distributions, relaxed shape (as found when in solution and also called solution shape), and normal modes and associated frequencies in solution or fixed at one or more points, as well as in response to external forcing.

In a first set of embodiments, a method includes receiving data that indicates a sequence of nucleotides on at least a first strand of a nucleic acid. The method also includes determining values for at least one physical property for each portion of the at least first strand. The method further includes determining, based at least in part on a numerical model and the physical properties for each portion, a value of at least one derived property of a nanostructure that comprises the at least first strand of nucleic acid.

In some of these embodiments, the method further comprises determining a difference between the value of the at least one derived property of the nanostructure and a target value of the at least one derived property. In some of these embodiments, if the difference exceeds the predetermined threshold, a change in the sequence of nucleotides on at least the first strand is determined based on the difference (e.g., to add or eliminate one or more crossovers to decrease or increase flexibility, respectively). In some of these embodiments, the method further includes determining, based at least in part on the numerical model and the physical properties for each portion, a revised value of at least one derived property of a revised nanostructure that comprises the change in the sequence of nucleotides and determining a revised difference between the value of the at least one derived property of the revised nanostructure and the target value. Thus, in some embodiments, information gained from the numerical model is used iteratively in order to optimize or improve one or more of the properties of the target DNA origami structure.

In other embodiments, a computer-readable storage medium or apparatus is configured to perform one or more steps of the above method.

Still other aspects, features, and advantages of the invention are readily apparent from the following detailed description, simply by illustrating a number of particular embodiments and implementations, including the best mode contemplated for carrying out the invention. The invention is also capable of other and different embodiments, and its several details can be modified in various obvious respects, all without departing from the spirit and scope of the invention. Accordingly, the drawings and description are to be regarded as illustrative in nature, and not as restrictive.

BRIEF DESCRIPTION OF THE DRAWINGS

The present invention is illustrated by way of example, and not by way of limitation, in the figures of the accompanying drawings and in which like reference numerals refer to similar elements and in which:

FIGS. 1G-1K are block diagrams that illustrate example solid shapes formed from one or more DNA molecules;

FIG. 3 is a block diagram that illustrates alternative finite elements for predicting properties of a DNA structure, according to another embodiment;

FIGS. 4A-4D are block diagrams that illustrate a method for predicting bending and twisting of a structure formed from DNA, according to various embodiments;

FIG. 5A is a flow chart that illustrates an example method for controlling properties of nucleic acid nanostructures, according to one embodiment;

FIG. 5B is a flow chart that illustrates an example method for determining the properties of a nucleic acid nanostructure in a step of the method of FIG. 5A, according to an embodiment;

FIG. 6 is a flow chart that illustrates an example method for preparing a nanostructure in another step of the method of FIG. 5A, according to an embodiment;

FIG. 7 is a block diagram that illustrates an example twisting shape of a nanostructure determined during the method of FIG. 5B, according to one embodiment;

FIGS. 8A-8D are block diagrams that illustrate multiple example bent shapes of corresponding nanostructures determined during the method of FIG. 5B, according to various embodiments;

FIG. 10A and FIG. 10B are graphs that illustrates multiple example vibrational normal modes of multiple vertical hexagonal lattice nanostructures determined during the method of FIG. 5B, according to one embodiment;

FIGS. 15B-15C are graphs that illustrate increased mechanical integrity (decreased flexibility) with increased number of crossovers for the example nanostructure of FIG. 15A, according to various embodiments;

DETAILED DESCRIPTION

A method and apparatus are described for controlling derived properties, such as relaxed shape, internal strains, or elastic properties of nucleic acid nanostructures. In the following description, for the purposes of explanation, numerous specific details are set forth in order to provide a thorough understanding of the present invention. It will be apparent, however, to one skilled in the art that the present invention may be practiced without these specific details. In other instances, well-known structures and devices are shown in block diagram form in order to avoid unnecessarily obscuring the present invention.

Deoxyribonucleic acid (DNA) is a replicating, usually double-stranded long molecule that encodes other shorter molecules, such as proteins, used to build and control all living organisms. DNA is composed of repeating chemical units known as "nucleotides" or "bases." There are four bases: adenine, thymine, cytosine, and guanine, represented by the letters A, T, C and G, respectively. Adenine on one strand of DNA always binds to thymine on the other strand of DNA; and guanine on one strand always binds to cytosine on the other strand and such bonds are called base pairs. Any order of A, T, C and G is allowed on one strand, and that order determines the complementary order on the other strand. The actual order may determine the effect of that portion of the DNA molecule. Information on a portion of one strand of DNA can be captured by ribonucleic acid (RNA) that also comprises a chain of nucleotides in which uracil (U) replaces thymine (T). Determining the order, or sequence, of bases on one strand of DNA or RNA is called sequencing. A portion of length k bases of a strand is called a k-mer; and specific short k-mers are called oligonucleotides or oligomers or "oligos" for short.

Some embodiments of the invention are described below in the context of scaffolded DNA origami comprising double helix structures with one or more Holliday junctions modeled using a finite element numerical model. However, the invention is not limited to this context. In other embodiments the shape and other properties are determined for single helix DNA or ribonucleic acid (RNA) structures, with or without Holliday junctions using finite element or other numerical models, such as finite difference numerical models. The proposed computational modeling framework may be applied to DNA/RNA structures that are internally stabilized mechanically using secondary small molecules such as synthetic nucleic acids, amino acids, etc., which are modeled using distinct physical properties in the finite element model. The computational framework uses physical modeling to predict DNA/RNA origami structural properties and shape, integrated with any one of a number of optimization algorithms that can be used with objective functions based on mechanics and other considerations such as financial cost of oligos in order to rationally design DNA/RNA-based structures.

Figure 1A:
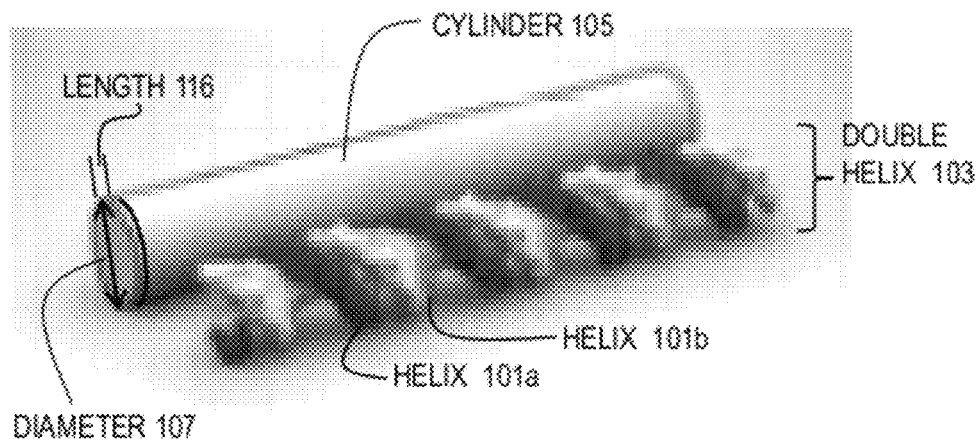
FIGS. 1A and 1B are block diagrams that illustrate multiple example representations of a portion of a DNA molecule, according to an embodiment.
Figure 1B:
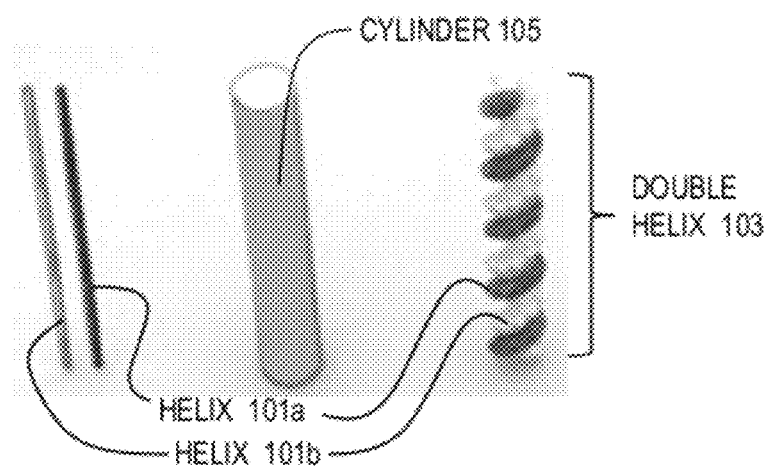

FIGS. 1A and 1B are block diagrams that illustrate multiple example representations of a portion of a DNA molecule, according to an embodiment. In FIG. 1A, a double helix structure 103 includes one strand of bases forming helix 101a and a second strand of bases forming helix 101b, all sharing the same central longitudinal axis. Though made up of the same nucleotides in complimentary sequences, helix 101a is rendered as dark in order to help visualize the spatial relationship between the two strands. The double helix 103 suggests a cylindrical volume, such as cylinder 105 with a diameter 107 and length that is a multiple of length 116 associated with the axial extent of one nucleotide. In a native configuration called B-form, one complete cycle of a helix around the axis corresponds to about 10.5 bases, e.g., two cycles corresponds to 21 bases. In FIG. 1B, the double helix 103 is depicted next to the cylinder 105. Also depicted is a linear representation in which the helix 101a and 101b are shown as parallel line segments, in essence a mental picture of the unwound strands of the double helix each offset equally from a central axis. For simplicity hereinafter the unwound helixes depicted in linear representations are called strands; even though, in situ, these strands are shaped as helixes.

Figure 1C:
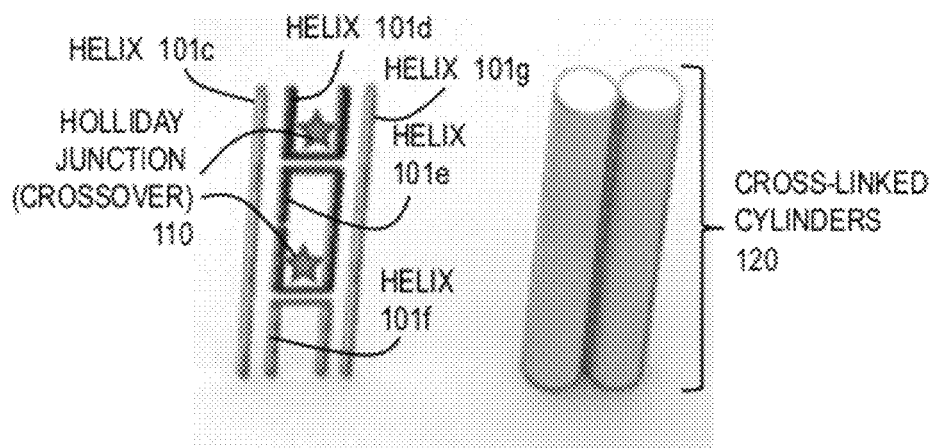
FIG. 1C is a block diagram that illustrates multiple representations of linked cylinders formed from one or more DNA molecules, according to an embodiment.

FIG. 1C is a block diagram that illustrates multiple representations of linked cylinders 120 formed from one or more DNA molecules, according to an embodiment. The linkage is best understood in a schematic representation of unwound parallel strands. Five strands are shown that link two cylinders to form cross-linked cylinders 120. The top few bases of strand 101c are paired with corresponding bases on a first portion of strand 101d, but not with a second portion of strand 101d. That second portion of strand 101d has bases that pair with the top few bases of strand 101g. Similarly, the next few bases of strand 101c are paired with corresponding bases on a first portion of strand 101e, but not with a second portion of strand 101e. That second portion of strand 101e has bases that pair with the next few bases of strand 101g. The four strands 101c, 101d, 101e and 101g form a Holliday Junction 110, also called a crossover 110. The crossover 110 causes adjacent cylinders to be attached, e.g., cross-linked. Without a second crossover, however, the cross-linked cylinders might not be parallel to each other. A second Holliday junction 110 formed by strands 101c, 101e, 101f and 101g attaches the cross-linked cylinders 120 at a second location, and causes the cylinders to be parallel, at least in the vicinity of the two depicted Holliday junctions 110.

Using a long scaffold DNA strand (e.g., over one thousand nucleotides) and multiple short staple DNA strands (e.g., less than one hundred nucleotides) that each hybridize with a different segment or segments of the scaffold DNA, cylinders can be arranged in sheets and blocks to form arbitrary shaped nanostructures. In DNA origami objects, individual DNA helices are connected to adjacent helices by multiple inter-helix connections (Holliday junctions). The inter-helix connections are formed by anti-parallel crossovers of either the staple or scaffold strand from one DNA helix to a neighboring one where the covalent phosphate backbone makes a U-turn between two consecutive bases at the crossover 110. In short-hand, inter-helix connections are drawn as thin lines running perpendicularly to the lines that represent strands. In the cylinder representation, such as dual cross-linked cylinders 120, crossovers are not drawn but their presence is implied by the alignment of neighboring cylinders.

Figure 1D:
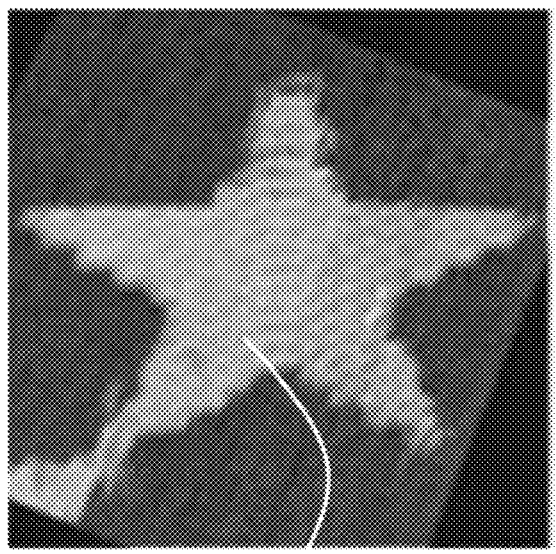
FIGS. 1D-1F are micrographs that illustrate example actual single-layer shapes constructed from a DNA molecule.
Figure 1E:
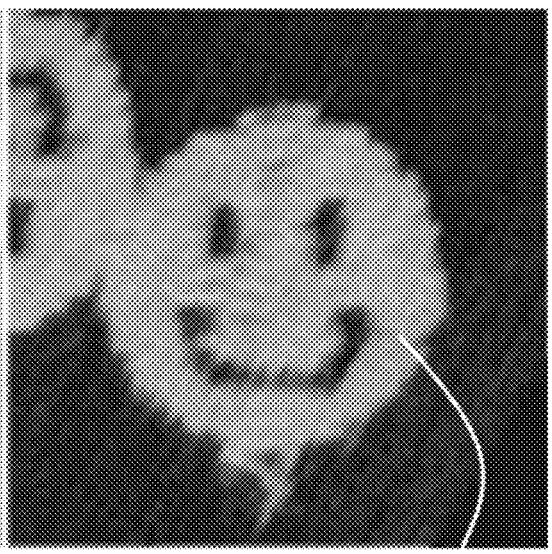
Figure 1F:
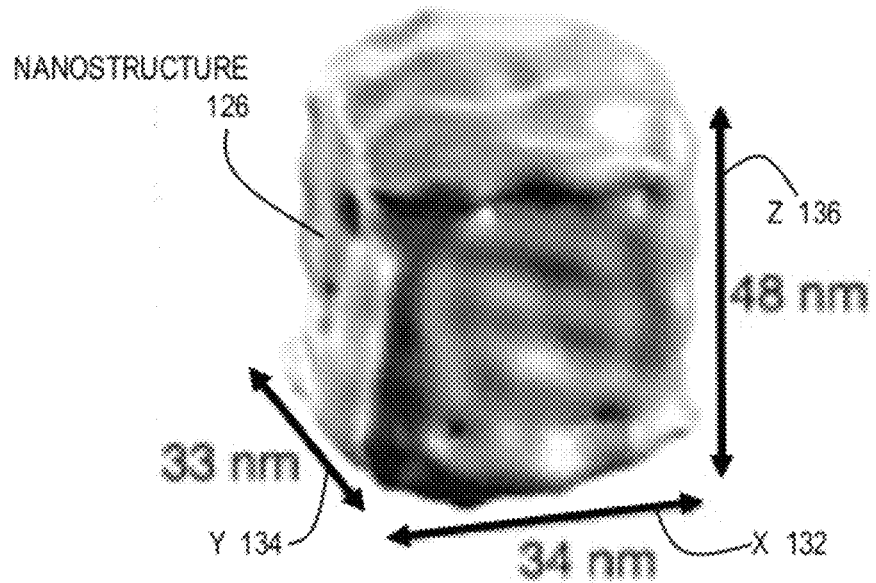

FIGS. 1D-1F are micrographs that illustrate example actual single-layer shapes constructed from a DNA molecule. These arrangement involves alignment of nucleotides of adjacent B-form DNA to cross link only every 21 nucleotides, or multiples thereof, when nucleotides on adjacent cylinders line up. Alternatively, these can be cross linked every 20 nucleotides by over winding the adjacent double helix about 5%; or every 22 nucleotides by under winding the adjacent double helix by about 5%.

FIG. 1D is a micrograph that depicts a star sheet nanostructure 122; and, FIG. 1E is a micrograph that depicts a smiley face sheet nanostructure 124. FIG. 1F is a micrograph that depicts a box nanostructure 126 made up of six sheets. In one horizontal direction indicated by X axis 132 the box nanostructure 126 is 34 nm long; in the perpendicular horizontal direction indicated by Y axis 134 the box nanostructure 126 is 33 nm wide; and in the vertical direction indicated by Z axis 136, the box nanostructure 126 is 48 nm high.

Figure 1G:
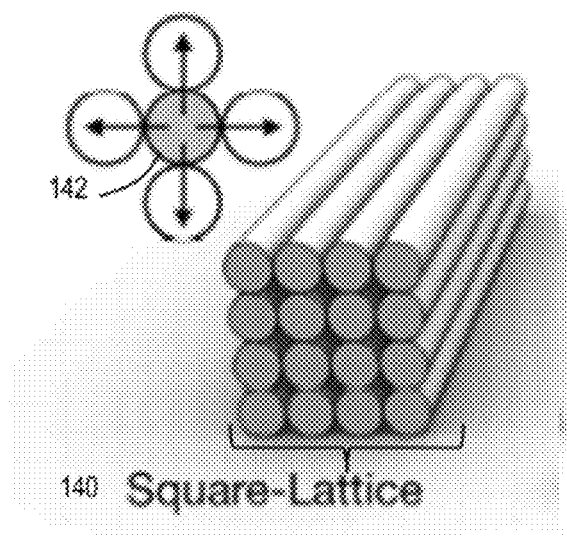
Figure 1H:
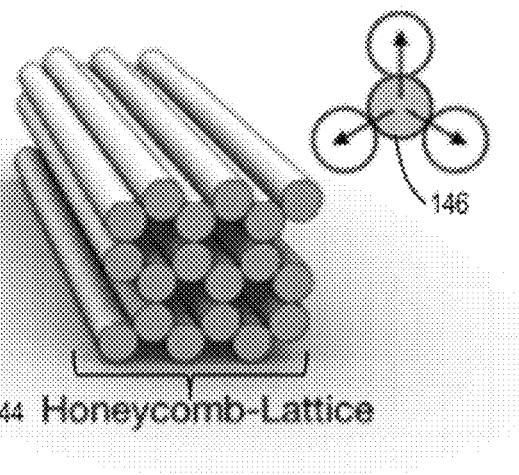

FIGS. 1G-1K are block diagrams that illustrate example solid shapes formed from one or more DNA molecules. Unlike sheets that occupy a volume with few cylinders, these solid lattices are capable of densely filling a volume with cylinders. FIG. 1G illustrates an example square lattice 140 in which each cylinder is cross linked at two or more Holliday junctions with each of four neighboring cylinders as indicated by insert 142. FIG. 1H illustrates an example hexagonal lattice 144 (also called a honeycomb lattice 144) in which each cylinder is cross linked at two or more Holliday junctions with each of three neighboring cylinders as indicated by insert 146.

Building custom space-filling multi-layer DNA origami shapes can be conceptualized as approximating the target shape by chipping away pieces from a solid block of DNA double helices that are bundled according to a certain cross sectional packing architecture (e.g., square lattice 140 or honeycomb lattice 144, which have been successfully used for building multi-layer DNA origami objects). In order to constrain individual DNA double-helices to a selected lattice position, both the square-lattice and the honeycomb-lattice rely on connecting neighboring helices with anti-parallel strand crossovers at Holliday junctions that occur periodically along the helical axis.

Figure 1I:
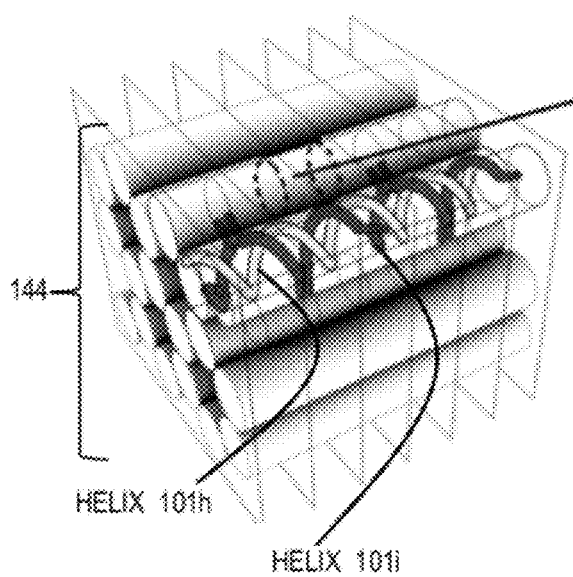

FIG. 1I provides a more detailed look into the internal architecture of a multi-layer DNA origami bundle in honeycomb-lattice 144 packing architecture. A B-form DNA double-helix has a natural helicity of 10.5 nucleotides (also called base pairs in a double helix arrangement) per full 360° turn (and thus 21 base pairs per 720°). This provides seven fold and three fold symmetry. A linear representation of 7 bases of a double helix is shown in FIG. 1I and a perspective view is depicted in FIG. 1J. Therefore, each strand of the double-helix (e.g., each of helix 101h and helix 101i) rotates by 240° about the helical axis every seven base pair as shown in FIG. 1K. When starting at a "high-noon" (12:00 pm) position on a 5' to 3' strand in a DNA duplex that is pointing away from the observer, seven base pair downstream the backbone of that strand will point to 08:00 pm, fourteen base pair downstream it will be at 04:00 am, and 21 base pair downstream it will be back at the high-noon position. Thus, a B-form DNA double-helix has a natural three-fold symmetry. In order to constrain DNA double helices to a honeycomb-lattice, one can naturally place crossovers in intervals of seven base pair to each of three possible neighboring helices without any a priori deviation from the default (average) B-form DNA helicity; and, with connections between two particular neighbors occurring every 21 base pair. This crossover spacing rule holds true for both scaffold and staple strands in a DNA double helix.

It is noted that the phosphate backbones of the two strands of opposite polarity in a double helix are pointing in nearly opposite radial directions at any given base pair position. Thus, in order to accommodate both scaffold and staple crossovers in a DNA origami object, one can define two separate crossover reference frames that are shifted by 5 base pair (corresponding to a backbone rotation of approximately 180°). When the staple strand on a chosen helix undergoes a crossover to a particular neighboring helix, the scaffold can undergo a crossover to the same neighbor only 5 or 16 base pair further down the helix, and other potential scaffold crossovers are similarly spaced in intervals of 21 bases from these locations.

By locally deviating from the 7-base pair crossover spacing periodicity when designing a DNA origami object with the honeycomb-lattice geometry, one can selectively cause local under- or over-twist as well as local tension or compression along axis. One may employ such local sources of mechanical strain (displacement per unit distance) as a design tool in order to produce, for example, shapes that exhibit a global twist deformation with desired handedness. One can also induce global bending deformations where curvature and bending angle can be finely controlled by creating an appropriate three-dimensional distribution of local sources of strain in a honeycomb-lattice DNA origami bundle.

A subtle detail distinguishes the square-lattice from the honeycomb-lattice. By default, the average B-form DNA double helix does not satisfy a 4-fold symmetry that is required in order to pack helices onto a square-lattice where each helix has up to four nearest neighbors. However, one may consider a slightly under wound version of B-form DNA with an average helicity of 10.67 base pair-per-turn. In this case, a four-fold symmetry emerges where the backbone of a strand rotates by 270° in intervals of 8 base pair. Thus, crossovers to four nearest neighbors in four-fold symmetry may be installed every 8 base pair, with crossovers to one particular out of the four neighbors being spaced in 32 base pair intervals. B-form DNA is sufficiently malleable to accommodate the under winding that is useful in order to build an object using the square-lattice approach. However, as a consequence of the local under winding to 10.67 base pair per turn, each of the helices in a square-lattice object will exert a small right-handed torque on its neighbors. These internal torques accumulate along the axis and result in a global twist deformation of the entire nanostructure.

Nanostructures built with the honeycomb-lattice architecture consistently appear straight, while the square-lattice nanostructures exhibit a global twist deformation whose extent depends on the aspect ratio and cross sectional area. Square-lattice objects with large cross sectional area (e.g., involving more than 20 helices) with an aspect ratio close to one tend to twist less than objects with high cross sectional aspect ratios or with smaller cross sectional areas. Single-layer square-lattice DNA origami objects with the default spacing of 16 base pair between crossovers to helix neighbors on the left and right, respectively, can be expected to assume a twisted shape in solution. Twist deformations may not be of concern, for example, when one is interested in shapes that find use when adhered to surfaces. Adhesion interactions may overrule the twist deformations; thus, resulting in objects that lay flat on a surface.

Thus, the square-lattice approach offers the appealing opportunity to create densely-packed shapes with rectangular features but it tends to result in globally twisted shapes. The honeycomb-lattice, in turn, by default creates straight albeit less-densely packed structures that can serve as controlled starting points for including additional shape complications, such as bending or twisting.

1. Overview

An approach is provided for quantitatively determining derived properties (including twisting, bending, stretching, or vibrational modes, internal strain energy, relaxed shape or some combination) of arbitrarily constructed nucleotide nanostructures (including scaffolded DNA origami nanostructures) and using those properties to converge on a design and fabrication process to generate nucleic acid nanostructures. This approach involves determining one or more finite elements or finite difference grid points that each represents physical properties of a portion of a nucleotide strand, such as one or more nucleotides. The approach further includes determining derived properties of the nanostructure based on the physical properties of the portions of one or more strands that make up the nanostructure. As used herein, a finite element refers to a data item that represents a value for at least one physical property for an atomic component of a structure, e.g., a component that is not further subdivided. There are a number of seemingly arbitrary choices as to what constitutes a finite element, from individual atoms, to combinations of atoms, to nucleotides, to base pairs of nucleotides, to strands, and choices as to what values to provide for the physical properties of those finite elements. Some choices have led to useful results that are corroborated by experiment, as described in more detail below.

In one approach, the fundamental volume element for determining derived properties of nanoparticles constructed with scaffolded DNA origami is a Watson-Crick base pair comprising one nucleotide on one strand of a double helix bound to the complimentary nucleotide on the other strand. The base pair can be considered as a cylindrical disc with a diameter 107 of about 2.2 nanometers and a height of one nucleotide having length 116 of about 0.33 nanometers.

Figure 2A:
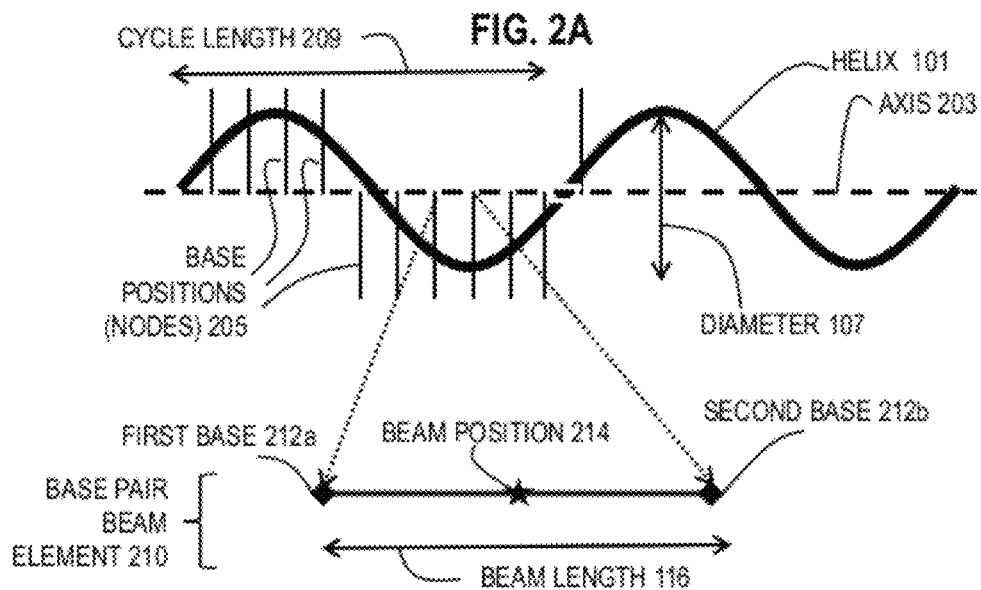
FIGS. 2A-2E are block diagrams that illustrate a finite element for predicting properties of a nucleic acid structure, according to one embodiment.

FIGS. 2A-2D are block diagrams that illustrate a finite element for predicting properties of a nucleic acid structure, according to one embodiment. In the illustrated embodiments, there is one finite element for each base in a single strand or each base pair in a double strand. FIG. 2A is a block diagram that illustrates an example relationship between a single strand helix 101 and a finite element, according to one embodiment. For a single strand, represented by helix 101 with diameter 107 centered around axis 203, there is a node 205 corresponding to the center position of each nucleotide (base) that intersects the helix 101. There are 10.5 nodes in one complete turn of helix 101, represented by helix cycle length 209.

In the illustrated embodiment, a finite element is a beam 210 that extends from the center of one nucleotide (first base 212a) to the center of the next nucleotide (second base 212b). The beam position 214 is the midpoint of the beam; and the beam has beam length 116. In other embodiments, a finite element is a beam that extends from one end of one nucleotide to the opposite end of the same nucleotide on the same strand. The nucleotide is centered at the midpoint of the beam. In embodiments of a finite element for a double helix, as described in more detail below, a finite element is a beam that extends from one end of one base pair linking the two strands to the opposite end of the same base pair. In each of these embodiments, the beam length 116 is the same.

Figure 2B:
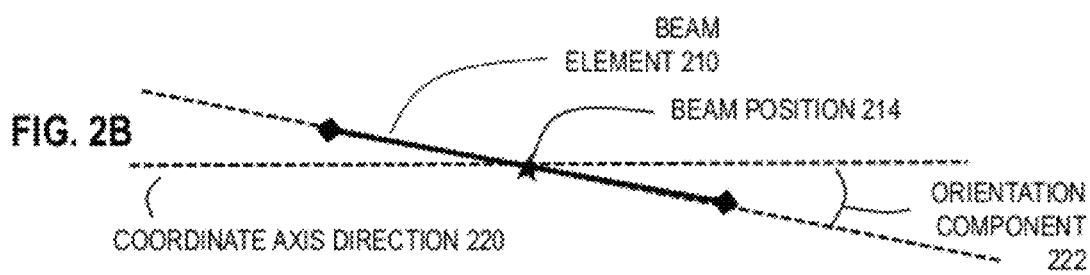

FIG. 2B is a block diagram that illustrates an example spatial coordinate system for locating beams in a finite element model, according to an embodiment. The beam (e.g., base pair beam 210) is located by three spatial coordinates for the center position 214 (e.g., three Cartesian coordinates or three polar coordinates) and the orientation of the beam is indicated by three angles relative to three coordinate axis directions. The orientation component 222 relative to one coordinate axis direction 220 is illustrated.

Figure 2C:
Figure 2D:
Figure 2E:

In any of these embodiments, the finite element is considered to be a beam with certain physical properties besides length 116. FIG. 2C is a block diagram that illustrates a bending spring constant kb, according to an embodiment. The spring constant kb indicates the resultant change in beam curvature as the beam deflects in response to a bending moment 230 (a force applied at a distance) that does not rupture the material element represented by the beam. Bending can be in either or both of two directions perpendicular to the axis of the beam. FIG. 2D is a block diagram that illustrates a twisting spring constant kt, according to an embodiment. The spring constant kt indicates the angle the beam twists in response to a twisting moment 240 that does not rupture the material element represented by the beam. FIG. 2E is a block diagram that illustrates a stretching spring constant ks, according to an embodiment. The spring constant ks indicates the distance the beam extends (or contracts) along the axis in response to a positive (or negative) stretching force 250 that does not rupture the material element represented by the beam.

While the example beam finite elements employed in this embodiment are mathematical representations that have zero cross sectional area themselves, each finite element represents a physical entity that does have an effective cross section with associated physical properties. An alternative embodiment uses fully three-dimensional finite elements that model the atomic-level shape and structure of DNA explicitly, but this would be computationally expensive. It is an advantage of the illustrated embodiment that substantially reduced computational effort is involved to model DNA origami structures with sufficient accuracy by using beams to represent bases in a single strand helix and base pairs in a double strand helix.

In some embodiments, the cross section of the physical element associated with the finite element is a function of the diameter 107 of the helix. For example, for a double helix the cross sectional area is the area of a circle with diameter equal to the helix diameter 107. For objects with finite cross-sections, the above spring constants lead to other common characterizations of elastic properties. With an area defined, the finite element has associated values for the moments of inertia (I for bending and J for twisting), Young's modulus (E) for elastic extension/compression, and Poisson's ratio ($\eta$). When a material is compressed in one direction, it usually tends to expand in the other two directions perpendicular to the direction of compression. Poisson's ratio $\eta$ is the ratio of the fraction (or percent) of expansion divided by the fraction (or percent) of compression, for small values of these changes. Symmetry or asymmetry in mechanical response may be chosen, for example to represent single-stranded DNA in stretching using a constant and positive E that is zero in compression.

In some embodiments, for a single strand helix, the cross sectional area is the same but the choice of spring constants, and the corresponding moduli are chosen differently, typically with much smaller values. For example, effective bending stiffness and twisting stiffness may be reduced to near zero compared to the double strand, whereas the axial stiffness may be chosen to be high in stretching and zero in compression in order to model the single-strand of DNA FIG. 3 is a block diagram that illustrates alternative finite elements for predicting properties of a DNA structure, according to another embodiment. In FIG. 3 alternative finite elements of a double helix with a Holliday junction are presented. Single strand base pair beam elements 310a, 310b, 310c, 310d, 310e, 310f, 310g, 310h, 310i, 310j (collectively referenced hereinafter as single strand base pair beam elements 310) each replicate the single strand base pair beam element 210 as shown in FIG. 2A to form two double helixes. The two strands are held together by hybridization binding forces 312 acting between complimentary bases on opposite strands. These hybridization forces stabilize DNA, whereas internal mechanical strain energy that is computed using the present finite element model competes to destabilize DNA. This information may therefore be used to maximize folding stability of a given DNA origami structure using programs such as RNASoft or SARSE that compute explicitly the hybridization free energy associated with DNA/RNA hybridization in a sequence-specific manner. To represent the Holliday junction, two single strand crossover structural beams 320 link the single strands in the different double helixes.

Thus, two adjacent DNA double helices in a bundle are connected by crossovers from either scaffold or staple strands, which are covalent phosphate linkages. In some embodiments, the movement of base pairs coupled by a strand crossover is described by a rigid body motion of the imaginary plane containing the cross-sections of those base pairs (the plane depicted in FIG. 3). This is modeled by connecting the end nodes of coupled base pairs using a rigid beam that has effectively infinite (in practice, a very large value of) stiffness as represented by large values of the spring constants kb, kt and ks. This crossover model is refined further, in other embodiments, as more experimental data that suggest the effect of crossovers to the bundle mechanics are available, for example, by allowing some smaller values of spring constants for certain deformation patterns.

In another embodiment, each beam element 314a, 314b, 314c, 314d (collectively referenced hereinafter as beam element 314) refers to a single complimentary base pair linking the two strands. The beam elements 314 are centered on the axial position of the corresponding base pair. The Holliday junction is then represented as a single crossover structural beam 324. Individual strands are not resolved in this embodiment. An advantage of this embodiment is the significant reduction in complexity and a commensurate increased speed in solving for the derived properties of the combined structure using the finite element model.

In other embodiments, a finite element represents multiple base pairs in a double helix, such as all the base pairs between adjacent Holliday junctions. For example, in some embodiments, a finite element beam represents 7 base pairs for B-form and honeycomb lattices, or 8 base pairs for square lattices.

When no insertions and deletions of base pairs are used in a nanostructure design, a three dimensional (3D) layout of helices describing the design (such as in the render panel of design tool caDNAno described below) describes, in principle, the final folded shape of the resulting nanostructure, except for cumulative twisting due to deviations from B-form winding.

However, further analysis is involved for prediction of the final relaxed shape when base pair insertions and deletions are used in the target design for globally bent and/or twisted bundle shapes. Although an actual path from unfolded to folded state is unknown, in some embodiments, it is treated as a mechanical process in which local internal strains in each helix induced by insertions and deletions are relieved by changing a global shape of DNA nanostructures through interactions between helices along the crossover beam elements.

FIGS. 4A-4B are block diagrams that illustrate a method for predicting bending and twisting of a structure formed from DNA, according to various embodiments. To model such bending and twisting from insertions or deletions, three representative configurations of DNA structures are introduced for computational analysis purpose, in some embodiments. The three configurations are termed: (1) an initial configuration, (2) a reference (strained) configuration, and (3) a final (relaxed) configuration.

In the initial configuration, double helices consist of unstrained base pair beam elements and the beam elements of adjacent double helices are not connected to each other. FIG. 4A depicts two double helix sections to be cross linked to induce a bend in the resulting nanostructure. Each section is considered for illustrative purposes to begin at a fixed end 402, although in reality this simply denotes some other part of the DNA structure that will have its own specific reaction forces (stretching, twisting, and bending) depending on the nature of the attachment. A standard double helix 412 has three base pair beam elements in a section before a planned Holliday junction. One double helix 414 has one extra base pair inserted, as indicated by a fourth base pair beam element. Another double helix 416 has one base pair deleted, as indicated by only two base pair beam elements. Note that three configurations become identical when no insertions and deletions exist in the design, and therefore the determinations described below become trivial.

The reference configuration represents the configuration that base pair beam elements are under strains, compressive/under-winding strain for insertions and stretching/over-winding strain for deletions, fit between crossover planes without a global shape change. FIG. 4B depicts the two double helix sections 414 and 416 forced to meet at a crossover 422 in a design crossover plane. The beam elements in double helix portion 414 with the extra base pair beam element have been compressed to shorten the portion 414 to the length of the standard portion 412. The applied force to achieve this shortening is determined automatically by the finite element model based on the stretching spring constant ks (or derived Young's modulus E) of the beam elements and the imposed length change and direction. The beam elements in double helix portion 416 with the deleted base pair beam element have been expanded to lengthen the portion 416 to the length of the standard portion 412. The applied force is determined automatically by the finite element model based on the stretching spring constant ks (or Young's modulus E) of the beam elements and the required length change and direction.

The final configuration is the relaxed configuration or which local strains of base pair beam elements are relieved through a global shape change of the double helix nanostructure, which is achieved by unloading the applied forces. If the forces and resulting displacements are small enough, the nanostructure is said to be in the linear range, and the forces are removed in a single step. FIG. 4C depicts the two double helix sections 414 and 416 in a bent configuration determined by releasing the forces and determining the resulting displacements.

It is generally true that forces in all directions change as the structure deforms due purely to changes in geometry. For small displacements, these effects are small. However, if the displacements are large enough, then the effective stiffness of the structure changes as the double helix deforms due to nonlinear geometric effects, and the components of the forces induced by deformation of the DNA along the compression direction changes as the bending angle changes. In some embodiments, the forces are relaxed incrementally and the resulting geometry shift used to again compute the effective spring constants. FIG. 4D depicts the two double helix sections 414 and 416 in a bent configuration determined by releasing the forces incrementally and determining the resulting displacement incrementally (as indicated by dashed lines) while considering geometry changes.

FIG. 5A is a flow chart that illustrates an example method 500 for controlling properties of nucleic acid nanostructures, according to one embodiment. Although steps are depicted in FIG. 5A, and in subsequent flow charts in FIG. 5B and FIG. 6, as integral steps in a particular order for purposes of illustration, in other embodiments, one or more steps, or portions thereof, are performed in a different order or overlapping in time, in series or in parallel, or are omitted, or one or more additional steps are added, or the method is changed in some combination of ways.

In step 501, the target derived properties of a nanostructure are determined, such as a target shape with one or more twists or bends, in whole or in part, or vibrational modes, or some combination. In some embodiments, target derived properties are not specified, and step 501 is omitted.

In step 503, a design to fabricate the nanostructure is determined, such as sequence of nucleotides on a nucleic acid molecule. For example, the sequence of nucleotides on a scaffold strand and the sequences of nucleotides on one or more staple strands are determined. Any method may be used to determine the nanostructure. For example, in some embodiments, based on detailed tutorials on how to design DNA origami shapes or based on an open source DNA origami design software called caDNAno that greatly facilitates the design of a vast spectrum of DNA origami shapes available on the World Wide Web (using the hypertext transfer protocol, HTTP) at domain name cadnano for domain name extension org, the design to fabricate the nanostructure is determined during step 503. In some embodiments, step 503 includes obtaining a design plan file that is formatted and output by caDNAno.

Thus step 503 includes determining a sequence of nucleotides on at least a first strand of a nucleic acid, or receiving data that indicates a sequence of nucleotides on at least a first strand of a nucleic acid. In some embodiments in which the nucleic acid is a double helix DNA, step 503 also includes determining a sequence of nucleotides on each of a plurality of short strands of deoxyribonucleic acid, wherein each short strand is complimentary to a unique portion of the first strand. In some embodiments, the staple strands are complimentary to different non-contiguous segments of the scaffold strand. Thus, in some embodiments, at least one short strand is complimentary to a unique but non-contiguous segment of the first strand.

The objective of this step is to conceive a target shape that can meet certain functional requirements. For example, in light of the intended applications one decides whether the object will be a multi-layer or a single-layer DNA origami structure and whether one will adopt a square-lattice or honeycomb-lattice architecture. 3D modeling software such as MAYA™ from AUTODESK, INC.™ of San Rafael, Calif., SKETCHUP™ from GOOGLE INC.™ of Mountain View, Calif., or TURBOCAD™ IMSI/DESIGN, LLC™, of Novato, Calif. may be of help for building and visualizing cylinder-models of the target structure. DNA origami offers the opportunity to divide the object into structural modules which can be built or changed separately. For example, a robot shaped DNA structure can be divided into three parts: a body, arms, and legs.

The design data is then retrieved, e.g., from caDNAno. For example, DNA structure design parameters include row and column indices of each double helix in the honeycomb lattice, the number of base pairs in each double helix, the location of inserted/deleted base pairs, and the location of scaffold/staple strand crossovers.

In step 505, the portions of the strands, such as the finite elements, corresponding to the design are determined. For example, in some embodiments, the finite elements 310 and 320 representing base pairs on individual strands, and the associated physical properties (such as length, cross-sectional area, moments of inertia and Young's modulus, or simply the corresponding effective spring constants, and rupture criteria) are determined. The rupture criteria allow for finite elements to model DNA rupture when local strain energies become relatively high. This rupture could entirely eliminate the local stiffness of the DNA, or only compromise/reduce one or more aspects of it (e.g., twisting and bending stiffness go to zero but extensional stiffness remains).

In the illustrated embodiment, the physical properties are determined for each base pair on the scaffold strand and the multiple staple strands that hybridize to the scaffold strand. In an illustrated embodiment, the finite elements 314 and 324 representing base pairs on corresponding strands of double helix DNA, and the associated physical properties are determined for each base pair of hybridized helices formed from the scaffold strand and multiple staple strands. In other embodiments, the finite elements representing multiple base pairs of the double helix between Holliday junctions, and the associated physical properties, are determined. Thus, step 505 includes determining values for at least one physical property for each portion of the at least first strand, or determining a finite element data item that indicates a value for at least one physical property of at least one nucleotide on a strand of nucleic acid. Furthermore, in some embodiments, during step 505 the finite element data item indicates the value for the at least one physical property of a plurality of base pairs of nucleotides of a double strand of deoxyribonucleic acid between successive Holliday junctions.

In some embodiments, described in more detail below, the finite element represents a value for the at least one physical property selected from a group comprising length, cross-sectional area, stretching spring constant (ks), bending spring constant (kb) and twisting spring constant (kt) or other parameters (such as moments of inertia and Young's Modulus) related to these spring constants, among others. These finite elements are arranged spatially according to the design of the double helix DNA expected to result from hybridizing the scaffold and staple strands. Thus, the finite element data item further indicates values for up to three translational degrees of freedom for a center position of the at least one nucleotide and three rotational degrees of freedom for an orientation of the at least one nucleotide.

In some embodiments, other physical effects are considered, such as electrostatic interactions of the charged DNA backbone, steric repulsion preventing overlapping in space, preference for dissolution in a polar medium like water (salvation energies), and rupture criteria (elastic limits for each spring constant), among others, in various embodiments. Thus, in various embodiments, the at least one physical property for each portion is selected from a group comprising length of the portion, stretching spring constant of the portion, bending spring constant of the portion, twisting spring constant of the portion, electrostatic charge of the portion, steric repulsion of the portion, salvation energy of the portion, and rupture criteria for the portion.

In step 507 the computed derived properties of the nanostructure are determined using the physical properties of the portions, such as the finite elements, determined in step 505 and a numerical model of mechanical interactions, such as a finite element model. The finite element model treats the nucleic acid structure (e.g., the DNA nanostructure) as a system of mechanical beams with bending, stretching, and twisting stiffness that is known experimentally; and, computes the deformed shape of the nanostructure by solving the mechanical equilibrium equations using the finite element method. Finite differences or another numerical discretization procedure are used in alternative embodiments, but finite elements are more computationally effective for beam modeling as used in the illustrated embodiments. Thus, in some embodiments, the numerical model is selected from a group comprising a finite difference model and a finite element model.

In the illustrated embodiment, the model is configured to additionally compute the normal mode shapes and associated frequencies of the nanostructure, in order to assess the mechanical stability of the structure, and to compute internal strain energies. The amplitudes of the normal mode shapes of the folded structure indicate the flexibility of the DNA structure under thermal fluctuations, and therefore whether it will be mechanically stable. The local elastic strain energy of the solution shape/deformed structure provides an indication of whether the hybridization energy will be sufficient to retain the structure in its folded form, or whether local rupture or lack of any folding whatsoever may occur. Direct calculation of derived properties due to active forcing is naturally also computed using the model, as well as alternative physical effects such as electrostatic interactions of the charged DNA backbone, steric repulsion preventing overlapping in space, and preference for dissolution in a polar medium like water (salvation energies), among others, in various embodiments. In the illustrated embodiment, computational efficiency is achieved by focusing on the first-order effects that are proposed to dominate in determining the solution shape and stability of DNA origami.

Any finite element model may be used. In an illustrated embodiment, the finite element model was implemented in ADINA™ from ADINA R&D, INC.™ of Watertown, Mass. Thus step 507 includes determining, based on a finite element computational model and the finite element data item, a value of at least one derived property of a nanostructure that comprises the first strand of nucleic acid. More details on step 507 are given below with reference to FIG. 5B. In some embodiments, the derived property of the nanostructure is selected from a group comprising length, shape, moment of inertia for bending, moment of inertia for twisting, Young's modulus, Poisson's ratio, internal strain energy distributions, and normal modes of vibration. Thus, step 507 includes determining, based at least in part on a numerical model and the physical properties for each portion, a value of at least one derived property of a nanostructure that comprises the at least first strand of nucleic acid. In these examples, the at least one derived property is selected from a group comprising relaxed shape, internal strain energy, normal modes of vibration, and stiffness.

In some embodiments, the model derives multiple solutions for the relaxed shape by taking different incremental steps to relax the reference forces non-linearly. For example, using different or random increments for releasing reference forces, a variety of relaxed shapes are determined with corresponding internal strain energies and normal modes. The results can then be presented probabilistically, with the most common shapes given higher weight than others. Additionally, in some embodiments, each shape is inversely weighted by the internal strain energy distributions that compete with folding free energy due to base-pair stacking interactions (i.e., favorable hybridization free energy).

In step 511, it is determined whether the computed derived properties satisfy the target derived properties for the nanostructure. For example, it is determined whether the shape, moduli or eigenvalues for associated normal modes of vibration, or internal elastic strain energy distribution, or some combination, computed for the nanostructure are within a predetermined absolute or percent tolerance of the target values of those properties. Thus, step 511 includes determining a difference between the value of the at least one derived property of the nanostructure and a target value of the at least one derived property. If the computed derived properties do not satisfy the target derived properties, e.g., are not within a predefined threshold, control passes to step 513 to change one or more of the nucleotide sequences used in the design determined during step 503.

In step 513, one or more of the nucleotide sequences used in the current design of the nanostructure is changed. For example a nucleotide is inserted or deleted in one or more of the scaffold strand and staple strands, e.g., to move a Holliday junction, to induce reduced or enhanced twist or bending, or both, to more closely resemble the target derived property. This change may be selected from a large number of alternatives using combinatorial or other optimization algorithms. The initial distribution of staples may also be chosen using such algorithms in order to obtain a first attempt of the desired target structure, after which the finite element analysis is performed to calculate values of derived properties, which are then used to inform/update the scaffold/stable design iteratively. Thus, step 513 includes determining a change in the sequence of nucleotides on at least the first strand based on the difference. Control then passes back to step 503 for determining the new sequences or to step 505 for determining the new corresponding finite elements, and to step 507 to compute the new derived properties of the nanostructure.

By repeated operation of the loop caused by steps 503 or 505, 507, 511 and 513, the computed derived properties are made to converge arbitrarily close to the target derived properties desired for the nanostructure. Following this loop provides the advantage of preventing the wasteful expenditure of resources, including time and money. For example, the computational loop prevents wasting resources making the dozens or hundreds of staple strands for scaffolded DNA origami only to find that the resulting structure always folds or includes appendages that constantly flop out of alignment in response to external vibrations or Brownian motion. Experimental yield of the folded target structure may also be maximized by minimizing internal strain energy distributions that compete with folding free energy due to base-pair stacking interactions (i.e., favorable hybridization free energy). Thus a repeat of step 505 and 507 includes determining, based at least in part on the numerical model and the physical properties for each portion, a revised value of at least one derived property of a revised nanostructure that comprises the change in the sequence of nucleotides. And a repeat of step 511 includes determining a revised difference between the value of the at least one derived property of the nanostructure and the target value.

When the computed derived properties satisfy the target derived properties, then control passes to step 521 to begin fabrication of the nanostructure. If no target properties are specified in step 501, or if step 501 is omitted, then all computed values are found to satisfy the target and control passes directly from step 507 to step 521.

In step 521 the constituent strands are prepared according to the final sequences that satisfy the target derived properties, including any fabrication or assembly of such component strands. For example, in scaffolded DNA origami, depending on the size of the scaffold template strand, a single DNA origami shape may require a few hundred unique staple strands (e.g., oligonucleotide sequences). The example 'robot' object involved 199 unique staple strands plus the scaffold strand. The in-house laboratory synthesis of these many different staple oligonucleotides is often not practical unless multiple DNA synthesizers running in parallel are available. High-throughput chemical synthesis of oligonucleotides on well plates including purification steps such as reverse-phase cartridge purification that largely remove truncated synthesis products is offered by a range of commercial vendors such as EUROFINS MWG OPERON™ of Huntsville, Ala., BIONEER, INC.™ of Alameda Calif., and ILLUMINA, INC.™ of San Diego, Calif. When ordering plate oligonucleotide synthesis one should consider ordering concentration-normalized oligos such that each staple oligonucleotide in each well is dissolved to the same concentration, for example 100 microMolar ($\mu M$, 1 $\mu M=10^{-6}$ Molar) concentration in either distilled water or in buffer. For convenience during later pipetting, it is advisable to group the staple oligonucleotides on the well plates according to the structural module to which they belong. For building the example robot-shaped structure, three 96-well plates were ordered. All the staple oligonucleotides that form the body of the structure are located on plate 1 and partially on plate 2, while the staples for building the limbs are found on plates 2 and 3.

Previous evidence shows that the quality of folding of DNA origami objects is affected by the choice of scaffold sequence. A number of custom-length variants of the M13 mp18 single-stranded bacteriophage genome have been tested and work robustly as templates for scaffolded DNA origami. Beyond the wild-type 7249 bases-long M13mp18 genome, variants of length 7308, 7560, 7704, 8064, and 8634 bases, respectively, have been cloned. Copies of these phage DNA for transfecting *E. coli* cultures and growing phage can be obtained from the Shih lab at Harvard Medical School, Boston, U.S.A., or alternatively, from the Dietz lab at Technische Universität München, Munich, Germany (the choice may be made based on shipping criteria). Single-stranded templates may also be prepared by enzymatic digestion of one strand in double-stranded plasmid DNA. Custom single-stranded templates have been produced by magnetic-bead separation of polymerase-chain-reaction amplicons as described elsewhere. Double-stranded templates that are separated during the assembly process itself have also been successfully used for building DNA origami shapes. However, folding complex shapes from double-stranded templates may prove more challenging than folding these shapes from single-stranded templates. Finally, an easy but cost-intensive way to prepare single-stranded scaffold DNA is to simply purchase it from vendors such as NEW ENGLAND BIOLABS™ of Ipswich, Mass., or BAYOU BIOLABS™ of Metairie, La. Once scaffold DNA has been purified or purchased, it should be aliquoted and stored at −20 degrees Celsius at a convenient standard concentration of for example 100 nanoMolar (nM, 1 nM=$10^{-9}$ Molar). An example robot shaped structure was folded from a previously reported 8064-bases-long variant cloned from the M13mp18 bacteriophage genome which was stored frozen at 100 nM concentration in 5 milliMolar (mM, 1 mM=$10^{-3}$ Molar) TRIS-Base and 1 mM EDTA at pH 8.

In step 523, one or more nanostructures are prepared based on the final constituent strands, such as the final scaffold strand and final staple strands for scaffold DNA origami, as prepared in step 521. Step 523 is a chemical self-assembly, called hybridization, as described in more detail below with reference to FIG. 6. Thus, step 523 includes preparing the nanostructure based at least in part on the first strand. If step 513 is performed, then step 523 includes fabricating the nanostructure based on the change in the sequence of nucleotides on at least the first strand, if the revised difference does not exceed the predetermined threshold. Thus step 523 includes fabricating the nanostructure based on the sequence of nucleotides on at least the first strand of the nucleic acid, if the difference determined in step 511 does not exceed a predetermined threshold.

In step 525, the nanostructures prepared during step 523 are utilized. For example the nanostructures are introduced into a biological system for diagnosis or treatment of conditions, or attached to a substrate for testing samples or providing functionalized surface of electronic or microelectromechanical systems (MEMS). In an illustrated embodiment, step 525 includes examining the nanostructures to determine the actual shape or stiffness or internal elastic strain energy distributions or vibrational modes of the nanostructure. Thus, in some embodiments, step 525 includes determining a measured value of the at least one derived property of the prepared nanostructure based on a measurement of the prepared nanostructure.

For example, extended DNA origami structures are imaged three-dimensionally using either negative-stain or cryogenic transmission electron microscopy (TEM) in various embodiments, while flat objects are conveniently imaged with atomic force microscopy. Shape heterogeneity is assessed on a particle-by-particle basis, in some embodiments. Image processing is used, in some embodiments, to identify systematic structural flaws or to reconstruct three-dimensional models from single-particle TEM data. Cryo-TEM has been used to reconstruct a 3D model of the single-layer fold-up box shown in FIG. 1F, while negative-stain TEM with 2% uranyl formate as staining agent has proved a to be a convenient tool for imaging stiffer multi-layer DNA origami objects.

The example 'robot' object was imaged with negative-stain TEM. For this nanostructure, it was observed that an arm on the left rested on the hip of the body part, with this configuration likely mediated by blunt end interactions between the top interface of a leg on the left and the lower interface of the arm on the left. In some images, one could hardly recognize an arm on the right which may be due to a folding defect in this region. Some image processing was performed in which multiple particle images were aligned and superimposed to yield an average image. The body and the legs appeared consistently folded as planned, while the arms of the object vanish in noise. This may be caused either by an elevated rate of folding defects in these parts of the structure or by a high degree of conformational flexibility and movement induced by thermal energy (which in the case of the example structure is likely to be the case). This kind of single-particle-based analysis is helpful to troubleshoot the structural details of a portion of a target nanostructure.

In some embodiments, step 525 includes mechanical testing of structure elastic properties or vibrational normal modes or internal strain energy distributions. Thus step 525 includes determining a measured value of the at least one derived property of the fabricated nanostructure based on a measurement of the fabricated nanostructure.

If a shape does not meet the set structural specifications, the workflow is restarted at step 513, where other internal scaffold/staple lay-out arrangements are worked out, or from step 523 where different hybridization conditions are tested. Pooling the staple molecules by structural modules facilitates exchanging staples for a particular part of the object that may need redesigning. In case of a satisfying result of the structural analysis, one moves to further processing or direct application in step 525, in various embodiments. Further processing may consist of assembling of multiple DNA origami objects into higher-order multimers (aggregates) or it may involve, for example, large-scale purification and concentrating the shapes to liquid crystalline conditions. In one such embodiment, purification produced DNA origami nanotubes that have found use as an alignment media for the structural analysis of membrane proteins by nuclear magnetic resonance.

In step 531, it is determined whether the physical properties or portions of strands, such as finite elements, should be refined. In some embodiments, the finite elements and the associated values are fixed and step 531 is omitted. If finite elements are not to be refined, or if step 531 is omitted, then in step 533 it is determined if end conditions are satisfied, such as closing a computer program implementing the method 500. If so, the process ends. Otherwise the process continues at step 501.

In some embodiments, physical properties or finite elements are to be refined. In these embodiments, control passes from step 531 to step 535. In step 535, systematic differences between computed and measured derived properties are taken as an indication that the finite elements or associated values are in error and should be revised, at least slightly. For example, values of physical properties of base pair beam 314 are revised. In some embodiments, it is determined in step 535 to change finite elements. For example beam elements 314 are replaced with single strand beam elements 312 for adjacent pairs of bases. In some embodiments, undetectable systematic differences between computed and measured derived properties are taken as an indication that the finite elements are smaller than needed to resolve the properties of interest and should be combined into larger elements, such as beams of 7 base pair length, or single beams between Holliday junctions, for faster computations. Control then passes to step 533, described above.

Thus step 535 includes determining a difference between the value of the at least one derived property of the nanostructure and the measured value. Step 535 also includes determining a change for the value for the at least one physical property of the portion or finite element based on the difference. This change may be selected from a large number of alternatives using combinatorial or other optimization algorithms. Thus step 535 includes determining a difference between the value of the at least one derived property of the nanostructure and the measured value; and determining a change for at least one value for the at least one physical property for at least one portion of the first strand based on the difference.

FIG. 5B is a flow chart that illustrates an example method 550 for determining the properties of a nucleic acid nanostructure in a step of the method of FIG. 5A, according to an embodiment. In step 551, the physical properties of each finite element (beam) are determined for each type of base pair. For example, they are retrieved from a local or remote database or determined as default values within computer code. In some embodiments, the beams have the same values regardless of the base or base pair that the beam represents. Thus, any nucleotide shares the same value for the at least one physical property. In some embodiments, different bases or base pairs are associated with one or more different values for a corresponding one or more physical properties.

During step 551, the values of length, diameter, kb, kt, ks are associated with each portion or finite element. In some embodiments, values of twist-stretch coupling parameter and Poisson's ratio η, are also determined during step 551. In an example embodiment, each beam finite element represents a bound base pair on each of the two strands of a double helix DNA molecule. In this embodiment, the values of the physical properties of the finite element beam are as described below, and include a length 116 of a base pair and diameter 107 of a double helix as depicted in FIG. 1A.

In step 553, the physical properties of each finite element (beam) are determined for each crossover, e.g., the physical properties for single strand crossover structural beam 320 or for double helix crossover structural beam 324. Thus, determining the finite element data item further comprises determining a first finite element data item and a different second finite element data item. The first finite element data item indicates the value for the at least one physical property of at least one nucleotide on a strand of nucleic acid in one double helix. The second finite element data item indicates a value for at least one physical property of a Holliday junction between adjacent double helices of a nucleic acid.

In step 555, one end of the structure is positioned in an arbitrary coordinate space. The elements aren't really "fixed" in coordinate space, the position and orientation is just chosen for convenience and all twists/extensions/etc. are relative to the crossovers before/after the current segment under consideration. For example, one end of the scaffold strand is fixed at coordinate (0,0,0) in three dimensional (3D) Cartesian coordinate space. In step 557 the coordinate of the next crossover is determined based on the design, e.g., based on the sequence of the scaffold strand and the sequence of the staple strand that best matches the beginning sequence on the scaffold strand. For example, the first crossover is at 7 base pair lengths along the x axis for a hexagonal lattice and 8 base pair lengths along the x axis for a square lattice, which is (7,0,0) and (8,0,0), respectively, in Cartesian coordinate space for the initial configuration that does not connect finite elements at crossovers (see FIG. 4A).

Thus, the finite element model is generated for each double helix in the initial configuration, where adjacent helices are not connected by crossovers yet. As described above, finite element nodes at boundaries in one side of a bundle of helices are placed first for each helix based on the helix location in the honeycomb lattice; and, then other nodes and elements are subsequently added along the helical axis for every base pair encountered. During this process, the reference coordinates of finite element nodes (the position vector and the cross-section orientation in twist angle) corresponding to the coordinates when there is no inserted or deleted base pair in the helix are also computed using L as the distance between neighboring nodes and Df=34.3 degrees as the end-to-end twist angle difference of a base pair that corresponds to a B-form DNA twist density of 10.5 base pairs per helix cycle. For example, if a node is generated for a normal base pair, both initial and reference coordinates of the node are increased by L and Df along the helical axis.

In step 561, it is determined if there are any unmatched insertions or deletions of base pairs on either of the two double helices to be linked at the crossover. If not, then in step 563 any net twist is accumulated for the section up to the crosslink. For example, if the crosslink is at 7 base pairs for two adjacent double helix portion at 240 degrees, as in a hexagonal lattice, then there is no net twist at the next crosslink. However, if the crosslink is at 8 base pairs for two adjacent double helix portion at 270 degrees, as in a square lattice, then there is a net twist due to under winding. Even though both adjacent double helices have the same number of base pairs up to the crossover, there is a net twist. Therefore, during step 561, determining the value of the derived property of the nanostructure based on the finite element computational model and the finite element data item further comprises determining whether adjacent double strands of a nucleic acid have a same number of nucleotide base pairs between adjacent Holliday junctions. If so, then in step 563, determining the value of the derived property of the nanostructure further comprises determining a net twist introduced between the adjacent Holliday junctions. Control then passes back to step 557 to find the coordinate of the next crossover.

If it is determined in step 561 that there are any unmatched insertions or deletions of base pairs on either of the two double helices to be linked at the crossover, e.g., that there are not the same number of base pairs to the crossover, e.g., that the x-coordinate values at the crossover are different on the two adjacent double helixes (see, for example, double helices 414 and 416 in FIG. 4A), then control passes to step 565. In step 565, displacements or rotations, or both, are applied to the nodes for the crossovers on the two double helices to bring them to the same coordinate, e.g., to the same x coordinate value and/or phi coordinate rotation angle value for torsion and/or theta coordinate rotation angle value for bending. Thus, the reference coordinates of a node generated for an insertion do not change while the reference coordinates for a deletion are increased (e.g., from 6,0,0 to 7,0,0) as if there exists a base pair; even though no beam or node is actually generated in the finite element model. This is performed in order to maintain geometric compatibility between connected/stapled helices. Also during step 565, the finite element model shifts to the reference configuration by displacing the nodes and twisting the cross-sections that are connected by strand crossovers to their reference coordinates computed as described above. Thus if there are 7 base pairs to the next crossover at coordinate (7,0,0) on one of the double helices and only 6 base pairs on the other at coordinate (6,0,0), a displacement is applied to the second to move the end of the second double helix from x coordinate 6 to x coordinate 7, thus aligning the ends of the two double helices. A solution step is then performed, e.g., in which the commercial finite element software program ADINA solves for the forces/torques involved to achieve these imposed displacements/rotations. Thus, in the illustrated embodiment, the initial configuration is strained to position Holliday junctions between adjacent double helix portions at a common distance along the axis, resulting in a reference configuration, such as depicted in FIG. 4B. The compression/expansion may be associated with a twist, e.g., an increased or decreased winding. For example, moving the end of the second double helix portion to coordinate (7,0,0) results in an unwinding of the second double helix and twisting force also applied at the end node.

In step 567, it is determined if there is another crossover in the design. If so, control passes back to step 557 to determine the coordinate of the next crossover. If not, then in step 569, any terminal base pairs dangling after the last crossover are added to the structure.

In step 571, a commercial finite element program is used to calculate the forces/torques resulting from the imposed displacements. In the second solution step a commercial finite element program is subsequently used to unload all imposed loads on the structure to obtain zero values throughout (reduce these external loads to zero). As a result, in the final finite element solution all external loads are zero and instead internal loads/reactions result due to the connectivity imposed by crossovers on helices. This analysis procedure may be performed using either the assumption of linear or nonlinear analysis, where the latter is desired for larger deformations. While no general criterion is established for when nonlinear analysis is preferable, an empirical test is performed whereby linear analysis is performed first, and subsequently nonlinear analysis as well. If the results (deformed shape) from the nonlinear analysis are the same as from the linear analysis, then the latter is not required. Otherwise, nonlinear analysis is desirable. As an alternative approach in some embodiments, linear analysis is performed and inter-helix distances between nodes connected by crossovers in the deformed structure are computed. If the maximum inter-helix distance exceeds a certain tolerance, e.g. 4*helix diameter (=4*crossover distance), nonlinear analysis is performed.

Thus, the deformation path from the externally strained configuration to the relaxed shape can be chosen to be either geometrically linear or nonlinear. It is assumed in linear analysis that displacements are infinitesimally small and the force equilibrium holds in the initial, un-deformed configuration. Accordingly, the final relaxed shape can be easily obtained in a single step without iterations. Therefore, in general, linear analysis is suitable when small deformations are expected from the relatively low density of insertions and deletions while nonlinear analysis is preferred when the targeted folded shape is achieved by large deformations.

If it is determined that any of the displacements are larger than some threshold for linear analysis, then in step 577 the force is released incrementally, e.g. a predetermined percentage of the original force is release in the next increment. In nonlinear analysis, the applied displacements are released gradually through several steps and the configurations where the external forces (due to the applied displacements) are equilibrated with the internal forces (due to strains in base pairs) are computed iteratively in each relaxation step. For example, initially 1% of the original force is released to compute an intermediate configuration. If no converged solution is found (suggesting too large a step is used), then 0.5% is used. If no converged solution is found again, then 0.25%, 0.125%, etc. are tried, until a converged solution is found. Hence, a more accurate relaxed shape is obtained for large deformations using a nonlinear analysis while it is computationally more costly depending on the amount of deformations. In step 579 it is determined whether there is another increment of reducing the applied forces. If so, control passes back to step 577. If not, control passes to step 573, described above to release any remaining forces. The final relaxed shape of the target design is computed in the loop between 577 and 579 and step 573 by releasing these applied displacements and rotations, but constraining adjacent helices by rigid (relatively very stiff) beams at crossover locations.

Thus, in steps 565 through 571 and step 577, determining the value of the derived property of the nanostructure based on the finite element computational model and the finite element data item further comprises, if the adjacent double strands of a nucleic acid have a different number of nucleotide base pairs between adjacent Holliday junctions, then determining a net bend and net twist introduced between the adjacent Holliday junctions. In some embodiments, determining the net bend and net twist introduced between the adjacent Holliday junctions further comprises applying a reference stretching force in step 565 to avoid a bend and, in step 577, subsequently relaxing the stretching force incrementally.

In step 575 the derived properties of the nanostructure are determined and presented, e.g., in data sent to a rendering process or a graphical user interface or some combination. For example, a 3D rendering of the bent and twisted nanostructure is presented in a graphical user interface. In some embodiments, the eigenvectors and eigenvalues of the solution set are also determined, which represent the vibration normal modes shapes and relative energies, respectively. In some embodiments, the internal elastic strain energy (due to twisting, stretching/compression, and bending) in the helices and crossovers are computed and either reported alone, or a rupture criterion imposed that releases the mechanical attachment between the joined helices. In some embodiments, external loads are applied to specific locations in the structure and its overall mechanical response calculated (e.g., overall stretching/twisting/bending stiffness of a bundle of helices). Equilibrium root-mean-square thermal fluctuations of the DNA structure may be computed directly from the normal modes and frequencies, as well as dynamical relaxation times if the DNA structure were coupled to a viscous fluid modeled by the Stokes equations and fluid-solid interaction finite element analysis. Thus, in some embodiments, step 575 includes presenting the derived property of the nanostructure to a user.

This embodiment of step 507 thus ends; and, control passes to step 511 of FIG. 5A as described above, to determine if the computed properties sufficiently match the target properties.

FIG. 6 is a flow chart that illustrates an example method for preparing a nanostructure in step 523 of the method of FIG. 5A, according to an embodiment. In step 601, at least some of the staple strands are pooled in proportions that support a particular number of replicates of each nanostructure (which may be a component of a nanostructure assembly). Pooling the staple oligonucleotides is conveniently accomplished with a multi-channel pipette. Equal amounts of concentration-normalized oligonucleotides belonging to a certain structural or functional part of the target structure are mixed to form a common pool. For the example robot shaped object three pools that contain the staple oligonucleotides that form the body, arms, and legs, respectively, were prepared. For further reference it is advisable to keep track of the number of staple oligonucleotides that go into each pool. For example, 126 oligos went into the 'body' pool, thus each of these oligos that were previously dissolved at 100 microMolar ($\mu M$, 1 $\mu M = 10^{-6}$ Molar) concentration in the well plate has now been diluted to 0.8 $\mu M$ effective concentration upon pooling. The staple pools produced at this step are combined in a modular fashion (for example, only body and legs) in volumetric ratios that reflect the number of staple oligonucleotides in each pool. For convenience, the combined pools are normalized such that each oligo is present at the same standard concentration of for example 500 nM. The combined pools are referred to as working stocks.

In some embodiments with complex structures, only the staple strands for the innermost portions of the structure are initially pooled during step 601. This is done to increase the yield. It is believed that yield of complex structures is diminished if hybridizations of the outer portions hinders the staple strands for the inner portions from obtaining access to the inner portions of the scaffold strand.

In step 603, the particular number of scaffold strands is added. In step 605, conditions favorable for hybridization are provided. Assuming correct sequence design, the target DNA origami structure is the only solution for the multi-component system of scaffold DNA and staple molecules that minimizes energy through Watson-Crick base pairing hybridization. However, whether the target structure indeed corresponds to the global energy minimum of the system will depend on solvent conditions and the design decisions that were taken in these steps.

For example, electrostatic repulsion between close-packed double-helices at low salt concentrations may counteract energy gain by hybridization. Similarly, internal elastic strains and stresses arising as a consequence of inappropriate scaffold or staple routing may outweigh energy gain by hybridization. The goal of the assembly reaction is to have the system equilibrate into a minimum energy state at conditions where this minimum corresponds to the target structure. A protocol that has robustly worked so far is to simply mix scaffold DNA and staple oligonucleotides in a fixed stoichiometry in a magnesium-containing solution during step 603, followed by subjecting the mixture to a thermal denaturation and annealing procedure during step 605.

Single-layer DNA origami shapes assemble much faster and with a lower defect rate than multi-layer shapes. The single-layer DNA origami assembly process may be likened to a self-solving two-dimensional jigsaw puzzle. The sequence by which the jigsaw puzzle is assembled matters only to a small extent. Many assembly pathways lead to the same final structure. In turn, the sequence of assembly matters quite a bit in the case of a three-dimensional jigsaw puzzle. Puzzle pieces in the interior of the three-dimensional object need to be placed first. By analogy, folding space-filling multi-layer DNA origami shapes can proceed along a multitude of assembly pathways that may not necessarily lead to the fully folded target structure but to partially folded dead-ends (kinetic traps) where parts of the structure need to disassemble again before further folding can proceed. For single-layer DNA origami shapes it is sufficient to mix all reagents, heat the mixture to 90 degrees Celsius and anneal it to room temperature over the course of a few hours. By contrast, folding space-filling multi-layer structures was observed to require annealing over the course of several days. Factors that affect the folding quality when using thermal annealing procedures are discussed elsewhere in detail. Isothermal chemical denaturation/renaturation for example by the addition of 85% formamide followed by slow dialysis against buffer is an alternative to thermal annealing.

A folding reaction contains scaffold DNA, staple DNA, water, pH stabilizing buffer, and additional ions (typically $MgCl_2$). Scaffold and staple DNA are added such that each staple is present in a defined stoichiometry relative to the scaffold, typically in a 5 to 10 fold excess. The working stock pools prepared in step 601 used in the folding reaction to assemble the entire object or only parts of it. The folding quality and yield of DNA origami objects is sensitive to $MgCl_2$ concentration. The optimal $MgCl_2$ concentration is identified by running a screen of concentrations and varies from structure to structure. Typically, optimal folding is observed in a range between 10 to 30 mM $MgCl_2$. The exact amount of $MgCl_2$ required may also depend on the staple oligonucleotide manufacturer likely due to differences in synthesis and purification protocols.

In some embodiments, folding three-dimensional DNA origami objects is enhanced by sequential addition of staple DNA molecules. In this way, the user may impose a specific folding pathway on the system that is less subject to kinetic folding traps. In these embodiments, the process 600 include steps 607 and 609 looping back to step 605. In step 607, it is determined if there are more staple strands to be introduced. If so, then in step 609 more of the staple strands are pooled for the correct number of replicates of each nanostructure (which may be a component of a nanostructure assembly). Control then passes to step 605 to allow the newly added strands to affect DNA folding.

For the case of the robot shaped nanostructure, a working stock was prepared in which all 199 staple oligonucleotides were present each at a 500 nM effective concentration. For the folding reactions, eight PCR tubes were filled with 20 micro liters (µl, 1 ml=$10^{-6}$ liters) of 100 nM scaffold DNA, 40 µl of the working stock with each staple at 500 nM, 10 µl of a folding buffer containing 50 mM TRIS-base, 50 mM NaCl, and 10 mM EDTA at pH 8, and 20 µl pure H20. The eight PCR tubes were then complemented each with 10 µl of a series of stock solutions containing 100, 120, 140, 160, 180, 200, 220, and 240 mM $MgCl_2$ dissolved in water to yield a set of eight folding reactions that contain scaffold and staples in a 1:10 stoichiometry and that sample effective $Mg^{2+}$ concentrations ranging from 10 to 24 mM $Mg^{2+}$ in 2 mM steps. The samples where then subjected to a thermal annealing ramp in a conventional PCR thermal cycler (TETRAD™ system from BIORAD LABORATORIES™ of Hercules, Calif.) that involves heating the mixture to 80° C., cooling it down to 60° C. with an incubation time of 5 minutes per temperature, followed by cooling it from 60° C. to 25° C. with an incubation time of 300 minutes per temperature. The whole annealing program took about seven days.

In step 611, the assembled nanostructures are separated from intermediate products and leftover reagents, such as by electrophoresis and purification steps. Evaluation of the quality of folding of DNA origami objects as well as purification of a desired species is conveniently accomplished by agarose gel electrophoresis. Agarose gels themselves and the running buffer are prepared to both contain magnesium to prevent denaturation of folded shapes. For space-filling multi-layer DNA origami objects it was found that for a given shape, the best folded nanostructures as judged by direct imaging by TEM were those that migrate with the highest speed through a 2% agarose gel. Thus, folding conditions (thermal ramps and buffer conditions) are optimized by searching for conditions that yield the fastest migrating species. Folding products are purified from agarose gel slabs simply by cutting out the desired bands, followed by crushing the gel slice with a pistol, and spinning it through a micro-column filter. This purification typically results in a solution containing about 2 to 5 nM of the target shape in addition to some left-over agarose traces. The yield of agarose gel purification varies with shape and there is still room for improvement. The example robot shaped nanostructure folded at 18 mM $MgCl_2$ was gel purified in this fashion.

This embodiment of step 523 thus ends; and, control passes to step 5251 of FIG. 5A as described above, to utilize the nanostructures.

2. Example Embodiments

In one example embodiment, a finite-element-based computational framework called 'CanDo' (for Computer-aided engineering for DNA origami) predicts scaffolded DNA origami 3D structures and evaluates their derived properties with single-base-pair resolution based on caDNAno design files. Thus, the finite element data item indicates the value for the at least one physical property of a single base pair of nucleotides of a double strand of deoxyribonucleic acid. CanDo parses caDNAno design files and models each base pair (regardless of type) as a two-node beam finite element (FE) that represents an elastic beam with effective physical properties that include geometric and material parameters. The geometric parameter values include length=0.34 nm and diameter=2.25 nm. The material parameters include stiffness parameters including values for stretch modulus=1100 picoNewtons (pN, 1 pN=$10^{-12}$ Newtons), bend modulus=230 pN $nm^2$, twist modulus 460 pN $nm^2$, and twist-stretch coupling=0, Stiffness refers to the force-displacement or torque-rotation relationships, and "modulus" refers to the material property chosen (Young's modulus, E, in axial stretching/ compression and bending, and shear modulus, G, in twisting). The stiffness parameters are then EA/L for the axial stiffness (A=area, L=length), EI for the bending stiffness that relates moment/torque to bending angle and GJ for the torque, where I and J are the appropriate second moments of area for the cross-section. While in reality each base pair may have up to four covalent phosphate linkages to neighboring helices, the mechanics of the DNA double helix is dominated by strong planar stacking interactions between neighboring base pairs.

Thus, the finite element model is simplified to a two-node finite element beam per base-pair. Each FE node has three translational degrees of freedom for the centerline of the cross-section and three rotational degrees of freedom for the orientation of the cross-section in torsion (one rotation about the axis) and bending (two rotations transverse to the axis). Strand crossovers defined in the caDNAno design file are modeled as either rigid constraints or compliant springs that connect end nodes of base pairs that are coupled by inter-helical crossovers. These springs can be used to model independently stretch, twist, and bend mechanical coupling introduced by crossovers.

To compute a 3D shape, CanDo first creates an initial configuration in which all base pairs as defined in the caDNAno source file are arranged linearly in space. In a second step, CanDo applies three fixed displacements on the first two nodes in a reference helix (two orthogonal fixed displacements, e.g., x and y, in one node and one orthogonal fixed displacement, e.g., z, in a second node) to eliminate three rigid body modes and two rigid body rotations of the overall structure. It then applies displacements and rotations to nodes so that crossovers may be modeled by connecting the nodes between neighboring base pairs in each double helix using rigid crossovers between helices. When using the square-lattice packing architecture or in the presence of deviations from the 7-base pair crossover spacing rule for the case of the honeycomb-lattice architecture (such as 8 base pair crossover spacing in square lattices), placement of these connections leads to internal strain in the object once the externally imposed displacements/rotations are removed/relaxed.

CanDo numerically determines the relaxed configuration of the object in which the external forces vanish. This is practically achieved by using either linear or non-linear analysis in which the FE nodes are displaced successively automatically using the finite element solver through several steps and the configurations where the external forces are equilibrated with the internal forces are computed iteratively in each step. CanDo performs the non-linear geometrical analysis using algorithms of a commercially available finite-element-analysis software called ADINA™ from ADINA R&D, INC.™ of Watertown, Mass.

The user obtains as output the deformed shape of the relaxed structure, as well as heat maps of the local magnitude of thermally induced fluctuations, which indicate flexibility in the relaxed structure. The user also obtains elastic strain energy maps that denote internal elastic strain energy in the structure In addition, CanDo computes the normal modes of the relaxed structure and provides the user with these deformed structures loaded with 1, 2, and 3 units of thermal energy. All output is provided in the *.bild data format, which can be visualized using freely available 3D viewers such as UCSF Chimera at subdomain cgl of domain ucsf with extension edu in directory chimera.

The utility of CanDo for predicting DNA origami 3D structures and for evaluating their flexibility is illustrated below. In its present form, CanDo is applicable to compact shapes such as those shown in FIG. 1D through 1H. In the future it will be extended to include designs with non-conventional connectivity such as wireframe structures. By using caDNAno and CanDo in an iterative manner of design and analysis, the design of sophisticated DNA origami shapes should no longer represent significant obstacles.

The preceding procedure implemented in CanDo to predict final relaxed shapes in solution that are affected by base pair insertions and deletions is applied to several DNA nanostructures designed for controlling global twist and bend.

To assess the model for the global twist, three versions of a 10×6 bundle (10-row-bundle with 6 double helices per row) are analyzed. Monomeric particles in its default version consist of 126 base pairs per double helix portion without any insertion or deletion that are fit into 19 crossover planes evenly spaced in 7-base pair steps corresponding to B-form, which is designed to induce no global twist. FIG. 7 is a block diagram that illustrates an example twisting shape of a nanostructure determined during the method of FIG. 5B, according to one embodiment. A portion 710 of the default monomer is depicted, showing all ten rows of 6 double helices per row, but only six of the 19 crossover planes (dark slices) every seven base pairs 707. The segments marked in orange in 710 indicate positions with deletions from 7 to 6 base pairs. This shows that having these site directed deletions induces twist. 730 is an ad-hoc model, while 720 is computed by CanDo.

Two other versions of monomers contain either six insertions or deletions in each double helix portion, corresponding to an average of 11 base pairs per turn or 10 base pairs per turn, respectively. Insertions induce locally compressed and under-twisted DNA which is designed to result in right-handed global twist of bundles while deletions induce locally elongated and over-twisted DNA which is expected to lead to the left-handed global twist. No bends are introduced because the same number of insertions and deletion are made on each double helix. Linear analysis for folded shapes of these monomeric particles shows that the correct handedness of each version of bundles is obtained. Monomer 712 with deletions shows the left-handed twist.

To quantify the twist angle, nonlinear analysis is performed for polymerized ribbons consisting of four monomers polymerized by adding a new set of single stranded DNA oligonucleotides whose sequences are designed to bind to single-stranded segments on head and tail interfaces on a monomer 721, thus bridging head with tail interfaces on each monomer. Different twist angles are obtained for bundles with 10, 10.5 and 11 base pairs per turn, respectively, that are matched within 20% to experimental measurements. The polymer 720 of four monomers with 10 base pairs per turn accumulates the left-handed twist; and, the structure 730 comprising more than nine monomers shows continued left-handed twisting.

The effect of unmatched insertions and deletions on globally bent shapes of DNA bundles has been explored by synthesizing seven versions of a slender-beam-like 3×6 bundle (3-row-bundle with 6 double helices per row) which is 420 base pairs long. FIGS. 8A-8D are block diagrams that illustrate multiple example bent shapes of corresponding nanostructures determined during the method of FIG. 5B, according to various embodiments.

The radii of curvature are controlled by gradients of insertions and deletions across the short axis of the cross-section between 15 out of 60 crossover planes in the middle to produce bend angles for every 30° from 0° to 180°. FIG. 8A depicts example rendered nanostructures 810, 820, 830 and 840 that exhibit bends of 0°, 30°, 60° and 90°, respectively, according to an embodiment. The density of insertions and deletions is balanced in order to prevent global twist; e.g., by maintaining the average of 10.5 base pairs per turn. Expected bend angles of these slender DNA bundles are obtained accurately using the present nonlinear analysis procedure. Despite large deformations of bundles, linear analysis also performs well in prediction of global bend angles within 20%, approximately up to 60°.

For nanostructures designed to bend more than 120°, however, displacements out of the bending plane are predicted due to severe local buckling in the middle of the structures which have not been observed in negative strain transmission electron microscopy (TEM) images of gel-purified particles. It is possible that high density of insertions and deletions localized in the middle of structures may induce local backbone or crossover breaks that relieve internal twist deformations, which is not considered in the illustrated embodiment of the FE model. In other embodiments, such breaks are accommodated by adding values for parameters that indicate strength and rupturing forces.

Figure 8B:
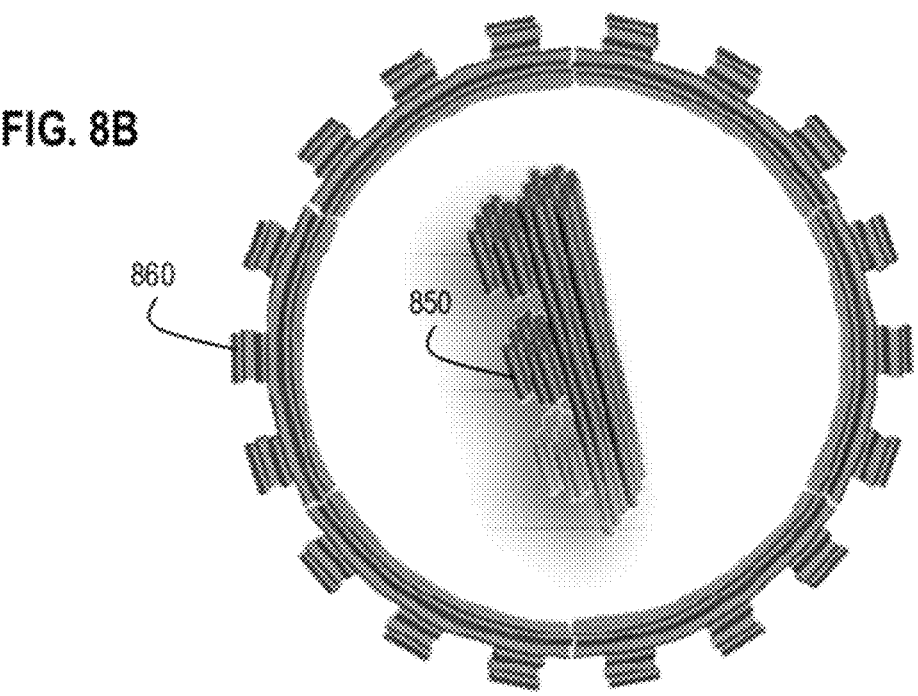
Figure 8C:
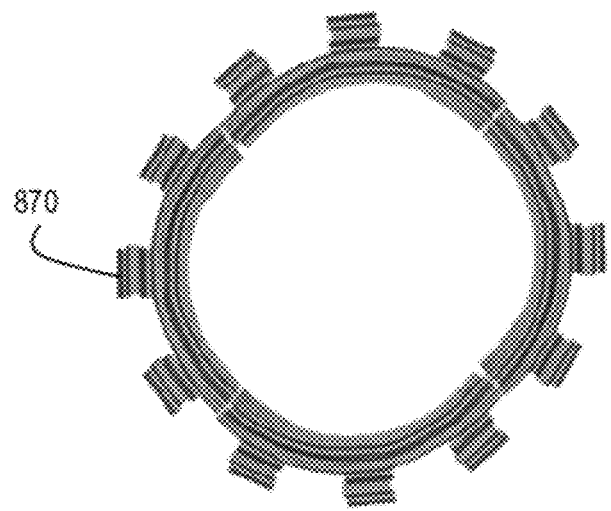
Figure 8D:
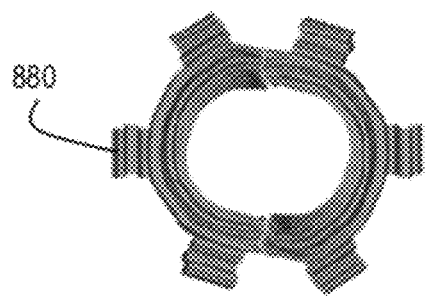

Controllable bent shapes of DNA bundles can be further utilized to build more diverse and complex curved shapes. For example, as shown in FIGS. 8B to 8D, several gear-like-bundles with different radius and number of teeth were synthesized by constructing and assembling DNA nanostructures 850 bearing three teeth folded in different bend angles. FIG. 8B is a diagram that illustrates an example 18-tooth gear in which each three-tooth section 860 is caused to bend 60°, according to an embodiment. FIG. 8C is a diagram that illustrates an example 12-tooth gear in which each three-tooth section 870 is caused to bend 90°, according to an embodiment. FIG. 8D is a diagram that illustrates an example 6-tooth gear in which each three-tooth section 880 is caused to bend 180°, according to an embodiment. Nonlinear analysis for these structures qualitatively predicts bend angles targeted in the designs.

The present DNA FE model is used to analyze mechanical characteristics of honeycomb-pleated rectangular blocks in seven different designs. There are two different ways of arranging helices in the honeycomb lattice to design DNA structures with similar cross-sectional dimensions: namely either vertically or horizontally oriented relative to an axis of symmetry of the lattice. The structures are different because the honeycomb lattice has 60 degree symmetry, and therefore slicing vertically and horizontally compared to an axis of symmetry produces very different arrangements. When the long axis is oriented vertically, 30 degrees from an axis of symmetry, hexagons formed by helices are staggered in the lattice; while they are aligned for horizontally oriented along an axis of symmetry. These differences particularly affect groove patterns of bundle surfaces. Also the scaffold pathways are different in two layouts along which scaffold strand crossovers exist. It is expected that these differences diminish when vertical and horizontal structures are cut from a square lattice.

Figure 9A:
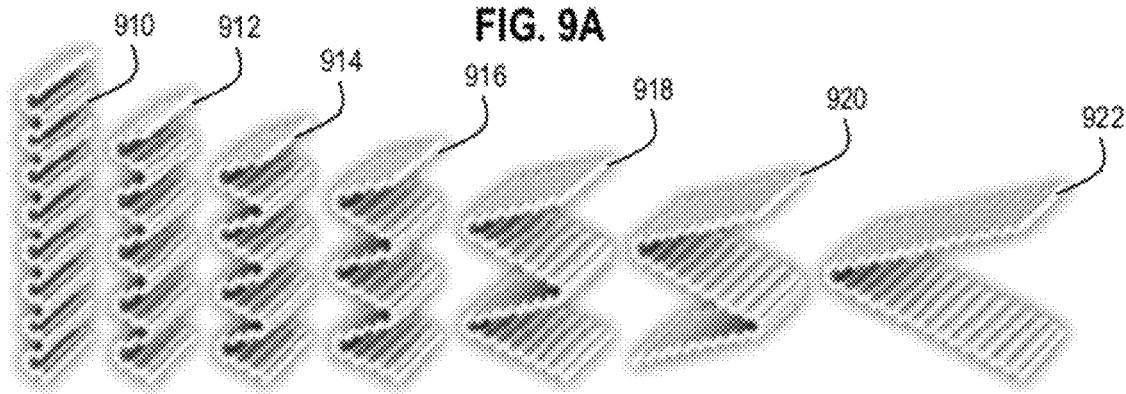
FIGS. 9A-9C are block diagrams that illustrate multiple example lattice shapes of corresponding nanostructures determined during the method of FIG. 5A, according to various embodiments.
Figure 9B:
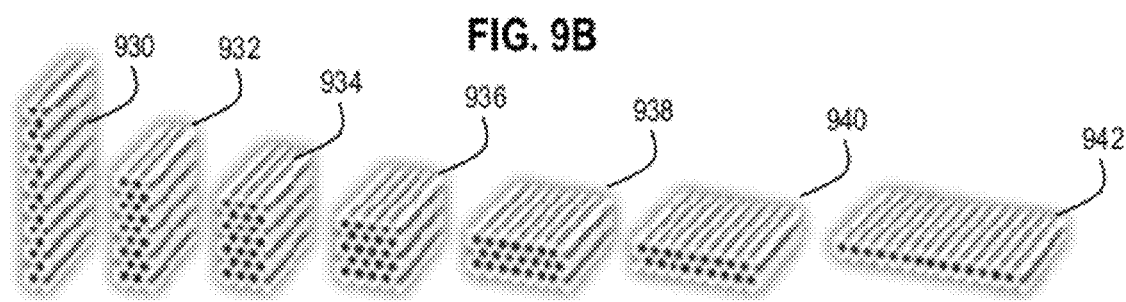
Figure 9C:
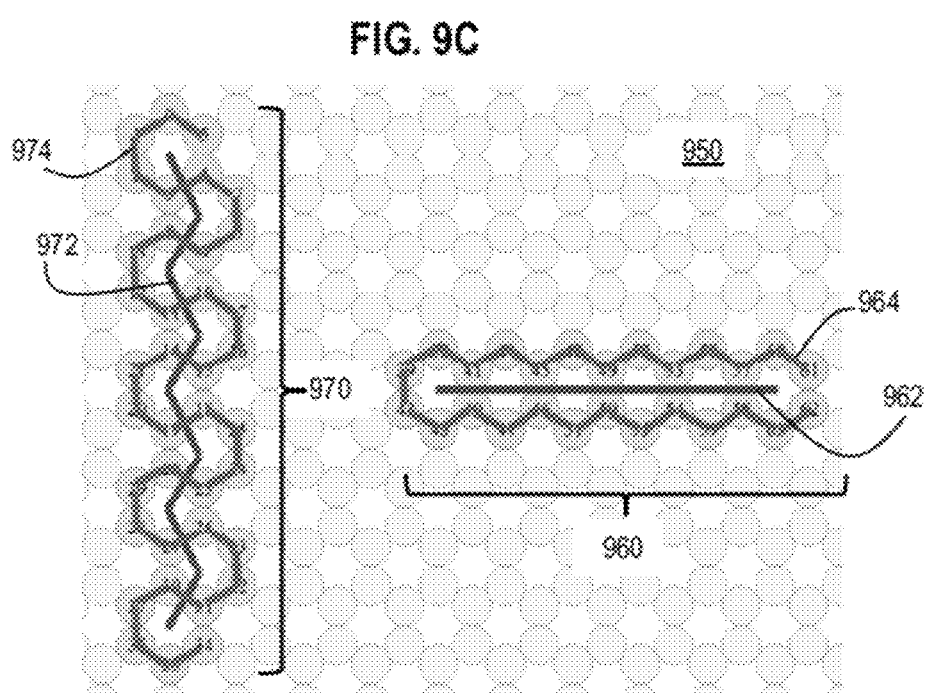

FIGS. 9A-9C are block diagrams that illustrate multiple example lattice shapes of corresponding nanostructures determined during the method of FIG. 5A, according to various embodiments. FIG. 9C is a diagram that depicts a honeycomb lattice 950, a horizontal cross-section 960 aligned with an axis of symmetry, and vertical cross section 970 that is 30 degrees from an axis of symmetry. The alignment of hexagon centers 962 along an axis of symmetry is straight, but the alignment of hexagon centers 972 is staggered 30 degrees from an axis of symmetry. The path of a scaffold 964 undulates slightly for a cross section aligned with the axis of symmetry, but the path of a scaffold 974 is much more convoluted at 30 degrees from an axis of symmetry.

FIG. 9A is a diagram that depicts seven honeycomb lattice nanostructure designs 30 degrees from an axis of symmetry; and FIG. 9B is a diagram that depicts seven corresponding honeycomb lattice nanostructure designs along an axis of symmetry for similar cross section. The seven nanostructure designs all include 60 to 64 parallel double helix portions each 126 base pairs long. The arrangements of these double helix portions in the seven designs are: 16×4, 10×6, 8×8, 6×10, 4×16, 3×20 and 2×30 as illustrated by rendered nanostructures 910, 912, 914, 916, 918, 920, 922, respectively, in FIG. 9A and by rendered nanostructures 930, 932, 934, 936, 938, 940, 942, respectively, in FIG. 9B. The nanostructures are designed to have no global deformation as neither insertions nor deletions are included.

Figure 10B:
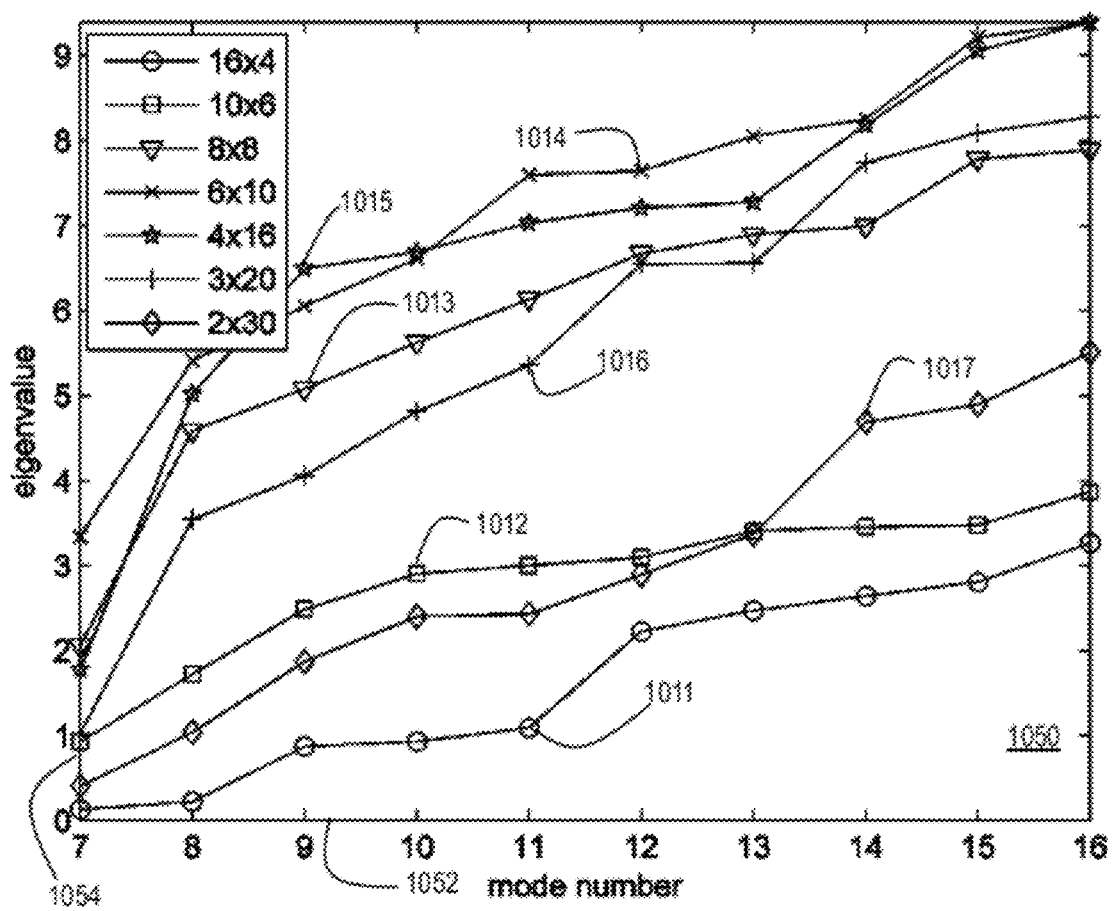
Figure 11A:
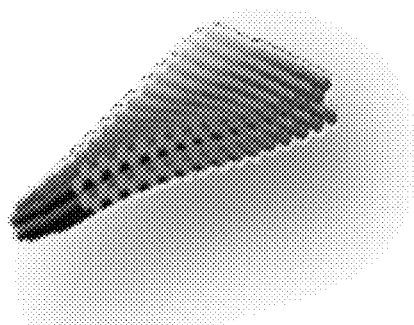
FIGS. 11A-11D are block diagrams that illustrate multiple example vibrational normal modes of an hexagonal lattice nanostructure based on the graph of FIG. 10A, according to one embodiment.
Figure 11E:
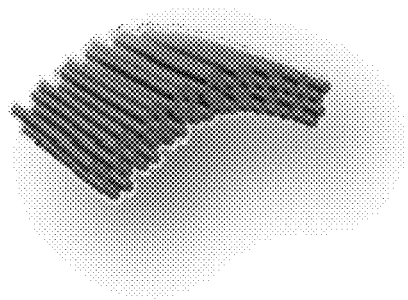
FIGS. 11E-11H are block diagrams that illustrate multiple example vibrational normal modes of a different hexagonal lattice nanostructure based on the graph of FIG. 10A, according to one embodiment.
Figure 11B:
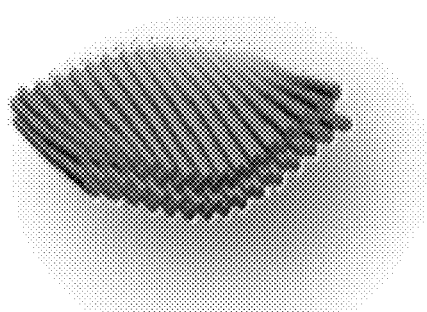
Figure 11F:
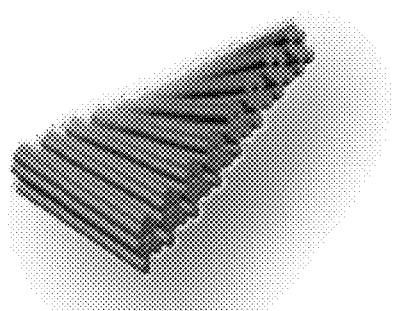
Figure 11C:
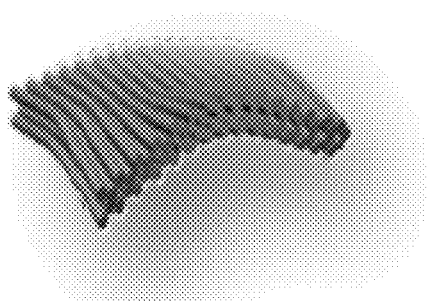
Figure 11G:
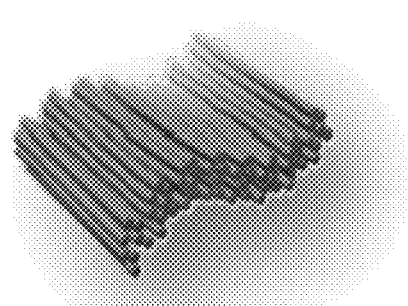
Figure 11D:
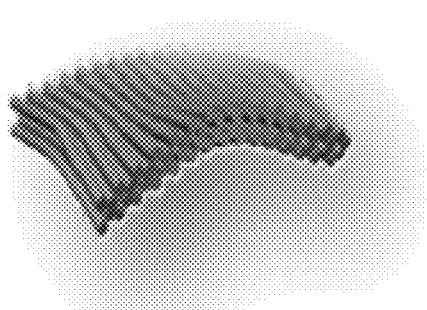
Figure 11H:
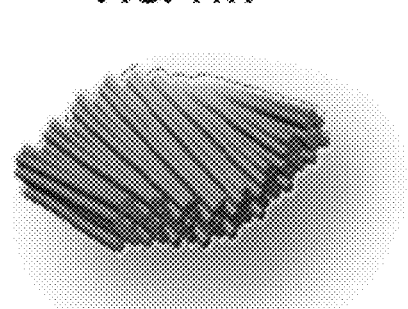
Figure 12A:
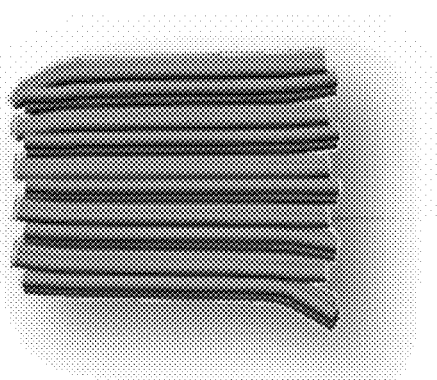
FIGS. 12A-12D are block diagrams that illustrate multiple example vibrational normal modes of helix tips without global deformations determined during the method of FIG. 5B, according to another embodiment.
Figure 12B:
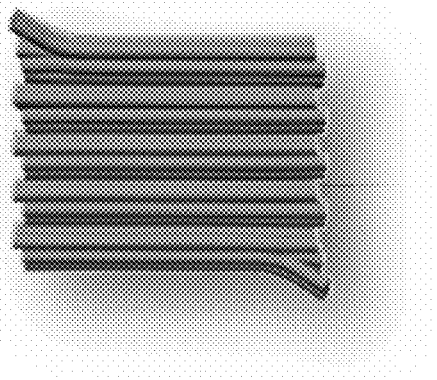
Figure 12C:
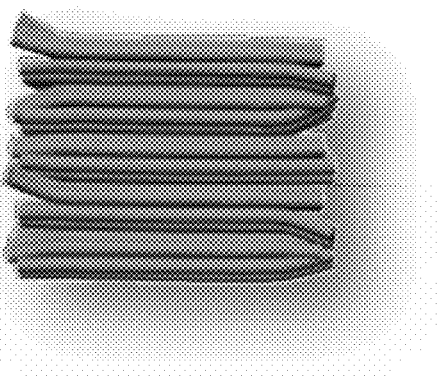
Figure 12D:
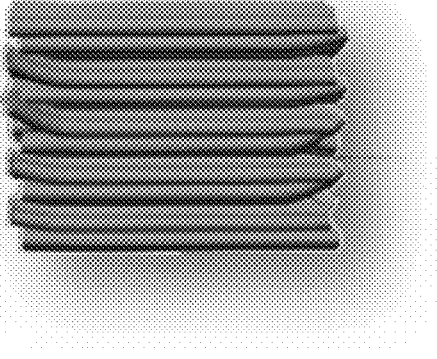

To investigate a potential effect of these differences on nanostructure derived properties, normal mode analysis is performed for the seven rectangular blocks in FIG. 9B aligned along an axis of symmetry. FIG. 10A and FIG. 10B are graphs that illustrates multiple example vibrational normal modes of multiple vertical hexagonal lattice nanostructures determined during the method of FIG. 5B, according to one embodiment. FIG. 10A is a graph 1000 that illustrates 46 vibrational normal modes. The horizontal axis 1002 indicates mode number, referring to an eigenvector, sorted in order of increasing eigenvalue. The vertical axis 1004 refers to the eigenvalue. The vibrational normal modes for the 7 nanostructures rendered in FIG. 9B are shown as trace 1011, trace 1012, trace 1013, trace 1014, trace 1015, trace 1016 and trace 1017, respectively.

Graph 1000 shows that all rectangular block designs of FIG. 9B have exactly six modes with zero eigenvalues that correspond to rigid body translations and rotations of the bundles that require no deformation energy. This indicates that helices are properly connected to each other so that at least some structural integrity is achieved. In general, eigenvalues increase linearly after these rigid body modes, which also appear typically when analyzing the conformational dynamics of proteins. Larger eigenvalues indicate the higher deformation energy that is involved and thus the corresponding mode is less likely to be activated under conditions of small thermal energy available.

FIG. 10B is a graph 1050 that zooms in on the first ten modes with non-zero eigenvalues from FIG. 10A. The horizontal axis 1052 indicates mode number; the vertical axis 1054 refers to the eigenvalue. The vibrational modes for the 7 nanostructures rendered in FIG. 9B are shown as trace 1011, trace 1012, trace 1013, trace 1014, trace 1015, trace 1016 and trace 1017, respectively, as in FIG. 10A. It is interesting that trace 1011 for 16×4 nanostructure and trace 1012 for 10×6 nanostructure exhibit relatively slow increase of eigenvalues compared with other nanostructures. In particular, the 16×4 nanostructure exhibiting trace 1011 is more flexible than the 2×30 nanostructure exhibiting trace 1017 despite their similar cross-sectional dimension.

FIGS. 11A-11D are block diagrams that illustrate multiple example vibrational normal modes of an hexagonal lattice nanostructure based on the graph of FIG. 10A, according to one embodiment. These are the lowest four non-zero vibrational modes for the 2×30 nanostructure 942. FIGS. 11E-11H are block diagrams that illustrate multiple example vibrational normal modes of a different hexagonal lattice nanostructure based on the graph of FIG. 10A, according to one embodiment. These are the lowest four non-zero vibrational normal modes for the 16×4 nanostructure 930.

The lowest mode of 2×30 nanostructure corresponding to the first global twist requires approximately three times the energy of the lowest mode of 16×4 nanostructure corresponding to the first global bend. Global bend and twist comprise the lowest modes of both bundles in common, but the bend about the helical axis is energetically favorable in 16×4 nanostructure where each helix remains straight but curved in relative location to each other. The bend about the long axis of the cross-section is favorable in the 2×30 nanostructure where each helix bends. Bent shapes of these blocks were also experimentally observed in TEM images that may be due to these structural modes of flexibility.

In the 10×6 bundle nanostructure exhibiting trace 1012, a plateau region appears in the eigenvalue profile. It turns out that modes in that region correspond to energetically similar local vibrations of helix tips at the edges of the block without global deformations. FIGS. 12A-12D are block diagrams that illustrate multiple example vibrational modes of helix tips without global deformations determined during the method of FIG. 5B, according to another embodiment. These are the plateau vibrational modes for the 10×6 nanostructure 932.

Figure 15A:
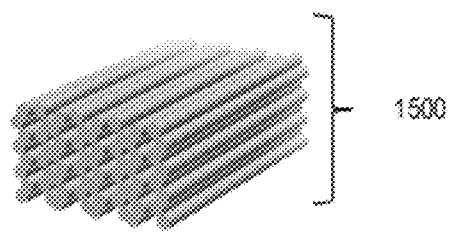
FIG. 15A is a diagram that illustrates an example nanostructure comprising a honeycomb lattice of cylinders, according to an embodiment.

The computer derived properties can be used to affect the design. For example, the number of crossovers can be changed in order to achieve a desired target flexibility or rigidity (mechanical integrity). FIG. 15A is a diagram that illustrates an example nanostructure 1500 of a honeycomb lattice of cylinders, according to an embodiment. In the illustrated embodiment, the nanostructure comprises a rectangular eight cylinder by eight cylinder honeycomb lattice of 7544 total base pairs and 1472 crossovers. The effect of eliminating various randomly distributed percentages of these crossovers can be determined in order to decide how many crossovers to include in a final design for the nanostructure.

Figure 15B:
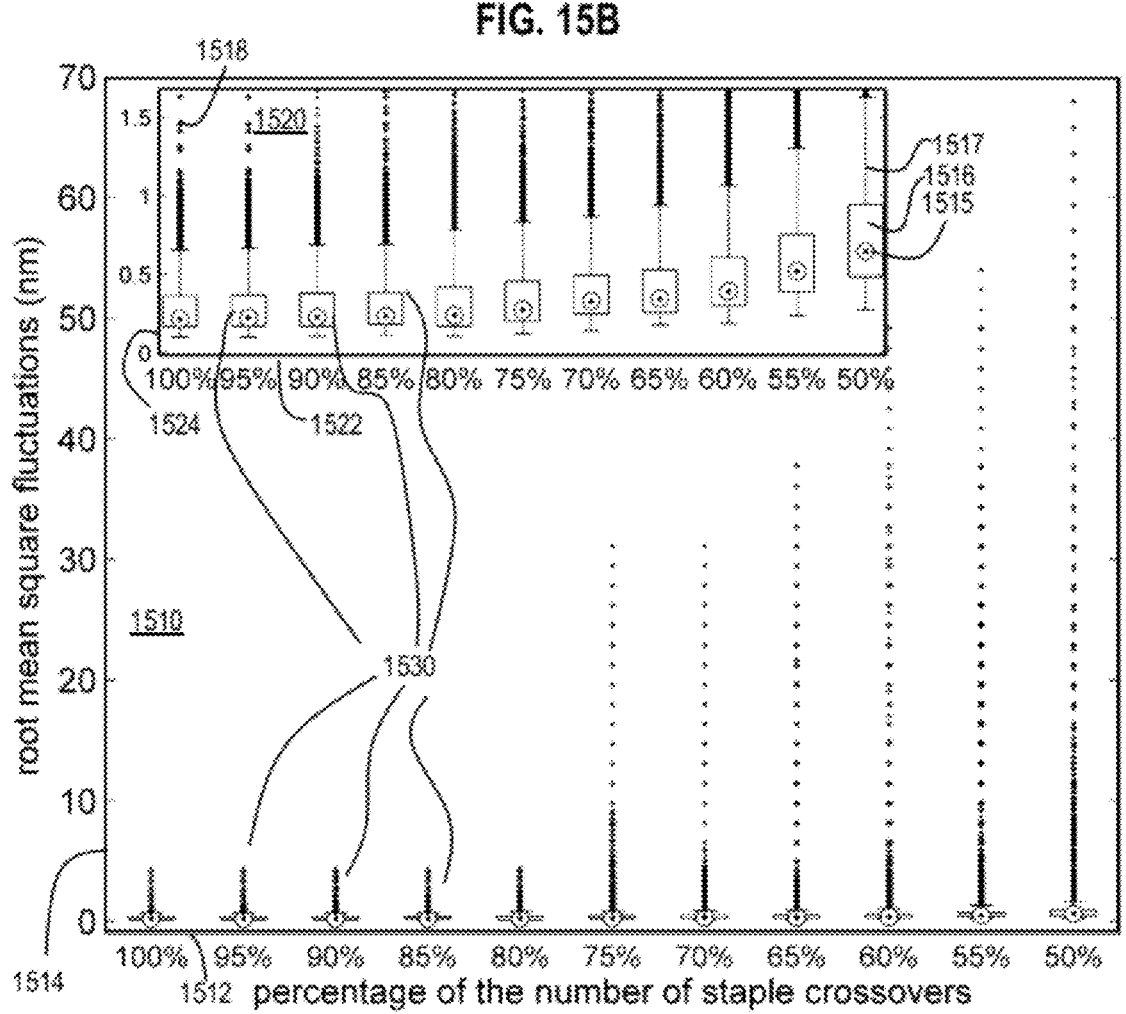

FIGS. 15B-15C are graphs that illustrate increased mechanical integrity (decreased flexibility) with increased number of crossovers for the example nanostructure of FIG. 15A, according to various embodiments. FIG. 15B is a graph 1510 that illustrates flexibility (decreased mechanical integrity) as a function of the percentage of crossovers. The horizontal axis 1512 is percentage of 1472 crossovers that are retained in an example nanostructure. The vertical axis 1514 is the root mean square fluctuations in nanometers (nm). Fluctuations are computed at each finite element by summing eigenvector magnitudes at the finite element; where eigenvectors are scaled such that each normal mode has the same amount of energy contribution to the total thermal energy. In the illustrated embodiment, each normal mode has one $k_B T$ of energy on average, which allows one theoretically to convert from normal modes to root-mean-square fluctuations (RMSF) of finite element nodes, where $k_B$ is the Boltzmann constant relating energy at the individual particle level with absolute temperature T observed at the collective or bulk level. Each percentage is represented by one simulated nanostructure with that percentage of crossovers randomly retained. Each point represents the fluctuations at one finite element in the simulated structure. The results 1530 for eleven different percentages spaced 5% apart from 100% to 50% are shown. More detail is provided for the more stable results (lower root means square fluctuations) in the inset graph 1520, with horizontal axis 1522 indicating percent of crossovers retained, and vertical axis 1524 for root mean square fluctuations in nanometers. The median value for all results at each percentage value is indicated by circle 1515, the $25^{th}$ and $75^{th}$ percentile value are indicated by vertical extremes of box 1516, and extreme values not considered outliers are indicated by vertical extremes of whiskers 1517. Rare values considered outliers are plotted as individual points 1518.

The statistical significance of these differences were also determined for these embodiments. FIG. 15C is a graph 1550 that illustrates flexibility (decreased mechanical integrity) as a function of the percentage of crossovers. The horizontal axis 1552 is the mean of the various values of root mean square fluctuations in nanometers (nm) depicted in FIG. 15B. The vertical axis 1554 is percentage of 1472 crossovers that are retained in an example nanostructure. One-way analysis of variance for comparing the means of root means square fluctuations (e.g., based on ANOVA1 & MULTCOMPARE functions in MATLAB) shows that the mean root mean square fluctuations of designs including less than 75% of staple strands (denoted by triangles 1558) are significantly different from those of other designs with higher percentage of included crossovers (denoted by circles 1556) suggesting onset of a significant change in the mechanical integrity of the nanostructures of similar shape and size.

The model produces strain energies that also can be used to adjust a nanostructure design. If the originally computed strain energies are undesirable, then the nanostructure is redesigned to distribute the strain energy differently, e.g., over more different base pairs or Holliday junctions, and the resulting strain energies are recomputed. The effect of distributing strain energies over more segments are depicted in the following diagrams.

Figure 16A:
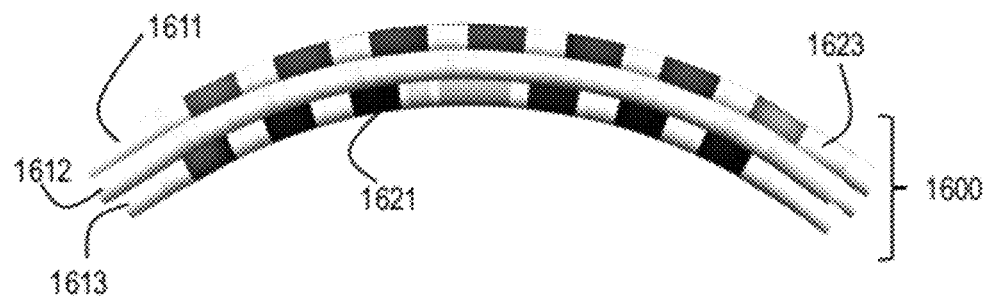
FIGS. 16A-16D are diagrams that illustrate the distribution of strain energies in a bent structure comprising three cylinders, according to an embodiment.
Figure 16B:
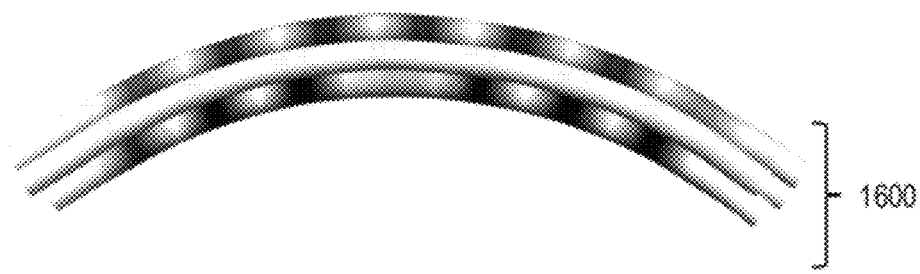
Figure 16C:
Figure 16D:

FIGS. 16A-16D are diagrams that illustrate the distribution of strain energies in a bent structure 1600 comprising three cylinders 1611, 1612, 1613, according to an embodiment. Strain is displacement per unit length and strain energy is the potential energy stored in bending the cylinder to a particular shape. High strain energy is indicated by dark shade (e.g., in segment 1621 in FIG. 16A) and low strain energy by light shade (e.g., in segment 1623 in FIG. 16A). The middle cylinder 1612 experiences relatively low strain energy. High strain energy is predicted on the top cylinder 1611 (due to tensile strain) and the bottom cylinder 1613 (due to compressive strain). FIG. 16A shows the strain energy with no averaging across multiple base pairs. FIG. 16B shows strain energies smoothed by averaging strain energies of the nearest 10 base pairs along each cylinder. FIG. 16C shows strain energies smoothed by averaging strain energies of the nearest 30 base pairs along each cylinder. FIG. 16D shows strain energies smoothed by averaging strain energies of the nearest 50 base pairs along each cylinder.

Figure 17A:
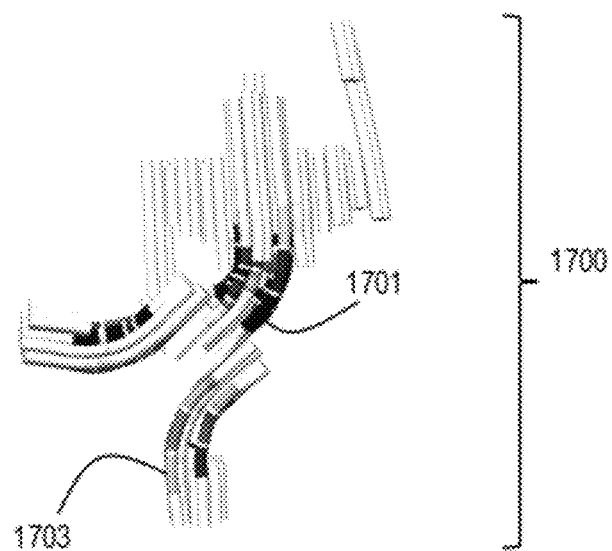
FIGS. 17A-17D are diagrams that illustrate the distribution of strain energies in a robot-shaped structure, according to an embodiment.
Figure 17B:
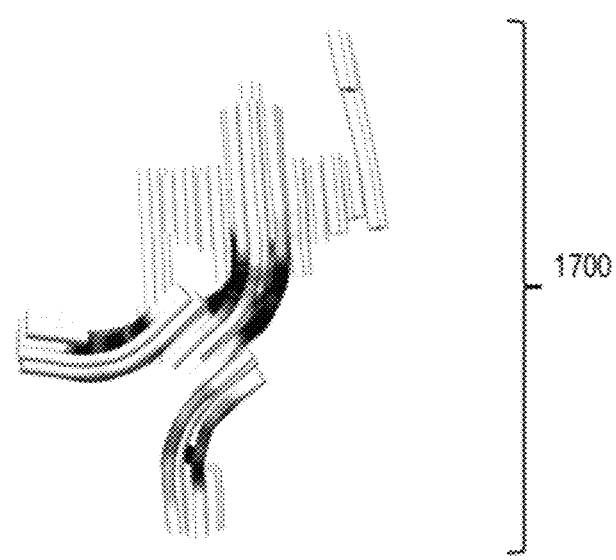
Figure 17C:
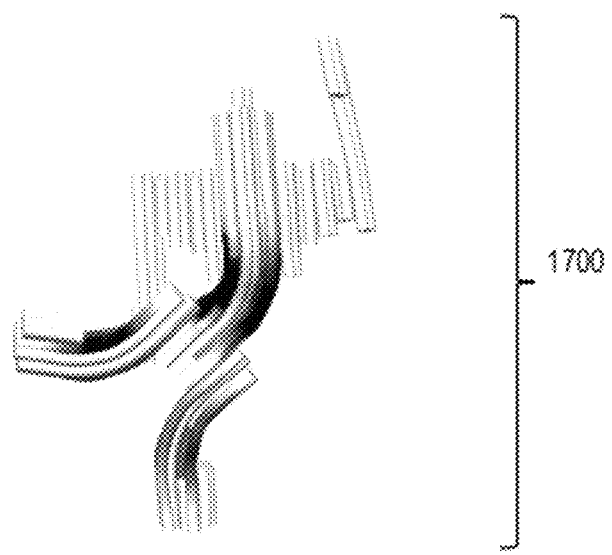
Figure 17D:
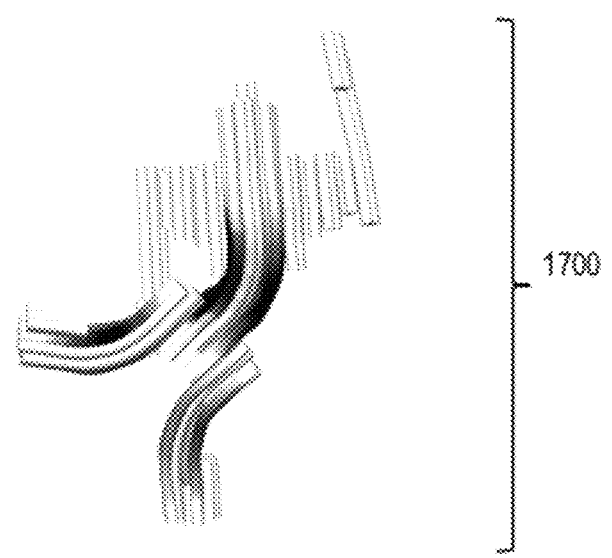

FIGS. 17A-17D are diagrams that illustrate the distribution of strain energies in a robot-shaped structure 1700, according to an embodiment. A segment 1703 near an ankle experiences relatively low strain energy. High strain energy is predicted at segments near a waist, such as segment 1701. FIG. 17A shows the strain energy with no averaging across multiple base pairs. FIG. 17B shows strain energies smoothed by averaging strain energies of the nearest 10 base pairs along each cylinder. FIG. 17C shows strain energies smoothed by averaging strain energies of the nearest 30 base pairs along each cylinder. FIG. 17D shows strain energies smoothed by averaging strain energies of the nearest 50 base pairs along each cylinder.

3. Hardware Overview

Figure 13:
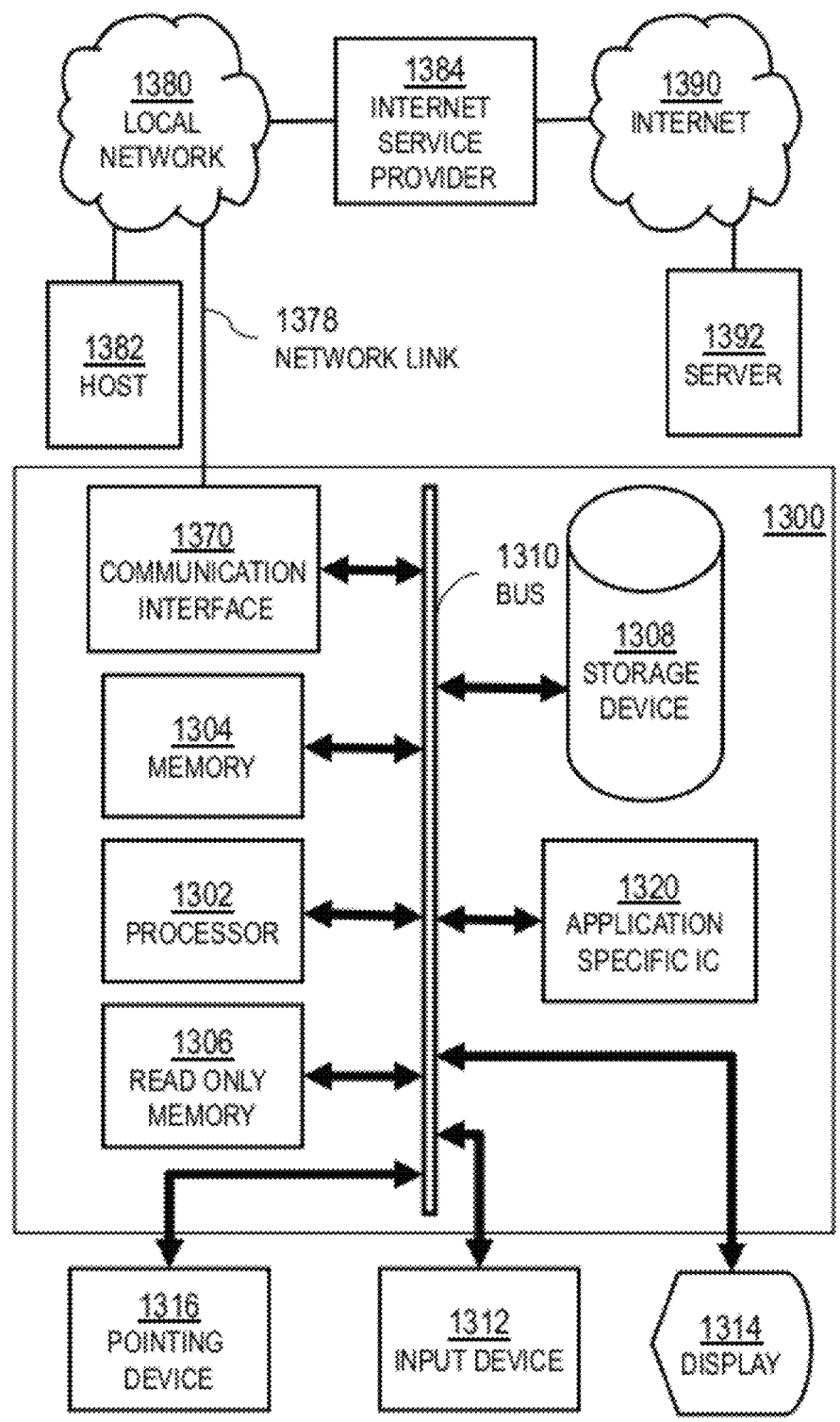
FIG. 13 is a block diagram that illustrates a computer system upon which an embodiment of the invention may be implemented.

FIG. 13 is a block diagram that illustrates a computer system 1300 upon which an embodiment of the invention may be implemented. Computer system 1300 includes a communication mechanism such as a bus 1310 for passing information between other internal and external components of the computer system 1300. Information is represented as physical signals of a measurable phenomenon, typically electric voltages, but including, in other embodiments, such phenomena as magnetic, electromagnetic, pressure, chemical, molecular atomic and quantum interactions. For example, north and south magnetic fields, or a zero and non-zero electric voltage, represent two states (0, 1) of a binary digit (bit). Other phenomena can represent digits of a higher base. A superposition of multiple simultaneous quantum states before measurement represents a quantum bit (qubit). A sequence of one or more digits constitutes digital data that is used to represent a number or code for a character. In some embodiments, information called analog data is represented by a near continuum of measurable values within a particular range. Computer system 1300, or a portion thereof, constitutes a means for performing one or more steps of one or more methods described herein.

A sequence of binary digits constitutes digital data that is used to represent a number or code for a character. A bus 1310 includes many parallel conductors of information so that information is transferred quickly among devices coupled to the bus 1310. One or more processors 1302 for processing information are coupled with the bus 1310. A processor 1302 performs a set of operations on information. The set of operations include bringing information in from the bus 1310 and placing information on the bus 1310. The set of operations also typically include comparing two or more units of information, shifting positions of units of information, and combining two or more units of information, such as by addition or multiplication. A sequence of operations to be executed by the processor 1302 constitute computer instructions.

Computer system 1300 also includes a memory 1304 coupled to bus 1310. The memory 1304, such as a random access memory (RAM) or other dynamic storage device, stores information including computer instructions. Dynamic memory allows information stored therein to be changed by the computer system 1300. RAM allows a unit of information stored at a location called a memory address to be stored and retrieved independently of information at neighboring addresses. The memory 1304 is also used by the processor 1302 to store temporary values during execution of computer instructions. The computer system 1300 also includes a read only memory (ROM) 1306 or other static storage device coupled to the bus 1310 for storing static information, including instructions, that is not changed by the computer system 1300. Also coupled to bus 1310 is a non-volatile (persistent) storage device 1308, such as a magnetic disk or optical disk, for storing information, including instructions, that persists even when the computer system 1300 is turned off or otherwise loses power.

Information, including instructions, is provided to the bus 1310 for use by the processor from an external input device 1312, such as a keyboard containing alphanumeric keys operated by a human user, or a sensor. A sensor detects conditions in its vicinity and transforms those detections into signals compatible with the signals used to represent information in computer system 1300. Other external devices coupled to bus 1310, used primarily for interacting with humans, include a display device 1314, such as a cathode ray tube (CRT) or a liquid crystal display (LCD), for presenting images, and a pointing device 1316, such as a mouse or a trackball or cursor direction keys, for controlling a position of a small cursor image presented on the display 1314 and issuing commands associated with graphical elements presented on the display 1314.

In the illustrated embodiment, special purpose hardware, such as an application specific integrated circuit (IC) 1320, is coupled to bus 1310. The special purpose hardware is configured to perform operations not performed by processor 1302 quickly enough for special purposes. Examples of application specific ICs include graphics accelerator cards for generating images for display 1314, cryptographic boards for encrypting and decrypting messages sent over a network, speech recognition, and interfaces to special external devices, such as robotic arms and medical scanning equipment that repeatedly perform some complex sequence of operations that are more efficiently implemented in hardware.

Computer system 1300 also includes one or more instances of a communications interface 1370 coupled to bus 1310. Communication interface 1370 provides a two-way communication coupling to a variety of external devices that operate with their own processors, such as printers, scanners and external disks. In general the coupling is with a network link 1378 that is connected to a local network 1380 to which a variety of external devices with their own processors are connected. For example, communication interface 1370 may be a parallel port or a serial port or a universal serial bus (USB) port on a personal computer. In some embodiments, communications interface 1370 is an integrated services digital network (ISDN) card or a digital subscriber line (DSL) card or a telephone modem that provides an information communication connection to a corresponding type of telephone line. In some embodiments, a communication interface 1370 is a cable modem that converts signals on bus 1310 into signals for a communication connection over a coaxial cable or into optical signals for a communication connection over a fiber optic cable. As another example, communications interface 1370 may be a local area network (LAN) card to provide a data communication connection to a compatible LAN, such as Ethernet. Wireless links may also be implemented. Carrier waves, such as acoustic waves and electromagnetic waves, including radio, optical and infrared waves travel through space without wires or cables. Signals include man-made variations in amplitude, frequency, phase, polarization or other physical properties of carrier waves. For wireless links, the communications interface 1370 sends and receives electrical, acoustic or electromagnetic signals, including infrared and optical signals that carry information streams, such as digital data.

The term computer-readable medium is used herein to refer to any medium that participates in providing information to processor 1302, including instructions for execution. Such a medium may take many forms, including, but not limited to, non-volatile media, volatile media and transmission media. Non-volatile media include, for example, optical or magnetic disks, such as storage device 1308. Volatile media include, for example, dynamic memory 1304. Transmission media include, for example, coaxial cables, copper wire, fiber optic cables, and waves that travel through space without wires or cables, such as acoustic waves and electromagnetic waves, including radio, optical and infrared waves. The term computer-readable storage medium is used herein to refer to any medium that participates in providing information to processor 1302, except for transmission media.

Common forms of computer-readable media include, for example, a floppy disk, a flexible disk, a hard disk, a magnetic tape, or any other magnetic medium, a compact disk ROM (CD-ROM), a digital video disk (DVD) or any other optical medium, punch cards, paper tape, or any other physical medium with patterns of holes, a RAM, a programmable ROM (PROM), an erasable PROM (EPROM), a FLASH-EPROM, or any other memory chip or cartridge, a carrier wave, or any other medium from which a computer can read.

Logic encoded in one or more tangible media includes one or both of processor instructions on a computer-readable storage media and special purpose hardware, such as ASIC ***1320.

Network link 1378 typically provides information communication through one or more networks to other devices that use or process the information. For example, network link 1378 may provide a connection through local network 1380 to a host computer 1382 or to equipment 1384 operated by an Internet Service Provider (ISP). ISP equipment 1384 in turn provides data communication services through the public, world-wide packet-switching communication network of networks now commonly referred to as the Internet 1390. A computer called a server 1392 connected to the Internet provides a service in response to information received over the Internet. For example, server 1392 provides information representing video data for presentation at display 1314.

The invention is related to the use of computer system 1300 for implementing the techniques described herein. According to one embodiment of the invention, those techniques are performed by computer system 1300 in response to processor 1302 executing one or more sequences of one or more instructions contained in memory 1304. Such instructions, also called software and program code, may be read into memory 1304 from another computer-readable medium such as storage device 1308. Execution of the sequences of instructions contained in memory 1304 causes processor 1302 to perform the method steps described herein. In alternative embodiments, hardware, such as application specific integrated circuit 1320, may be used in place of or in combination with software to implement the invention. Thus, embodiments of the invention are not limited to any specific combination of hardware and software.

The signals transmitted over network link 1378 and other networks through communications interface 1370, carry information to and from computer system 1300. Computer system 1300 can send and receive information, including program code, through the networks 1380, 1390 among others, through network link 1378 and communications interface 1370. In an example using the Internet 1390, a server 1392 transmits program code for a particular application, requested by a message sent from computer 1300, through Internet 1390, ISP equipment 1384, local network 1380 and communications interface 1370. The received code may be executed by processor 1302 as it is received, or may be stored in storage device 1308 or other non-volatile storage for later execution, or both. In this manner, computer system 1300 may obtain application program code in the form of a signal on a carrier wave.

Various forms of computer readable media may be involved in carrying one or more sequence of instructions or data or both to processor 1302 for execution. For example, instructions and data may initially be carried on a magnetic disk of a remote computer such as host 1382. The remote computer loads the instructions and data into its dynamic memory and sends the instructions and data over a telephone line using a modem. A modem local to the computer system 1300 receives the instructions and data on a telephone line and uses an infra-red transmitter to convert the instructions and data to a signal on an infra-red a carrier wave serving as the network link 1378. An infrared detector serving as communications interface 1370 receives the instructions and data carried in the infrared signal and places information representing the instructions and data onto bus 1310. Bus 1310 carries the information to memory 1304 from which processor 1302 retrieves and executes the instructions using some of the data sent with the instructions. The instructions and data received in memory 1304 may optionally be stored on storage device 1308, either before or after execution by the processor 1302.

Figure 14:
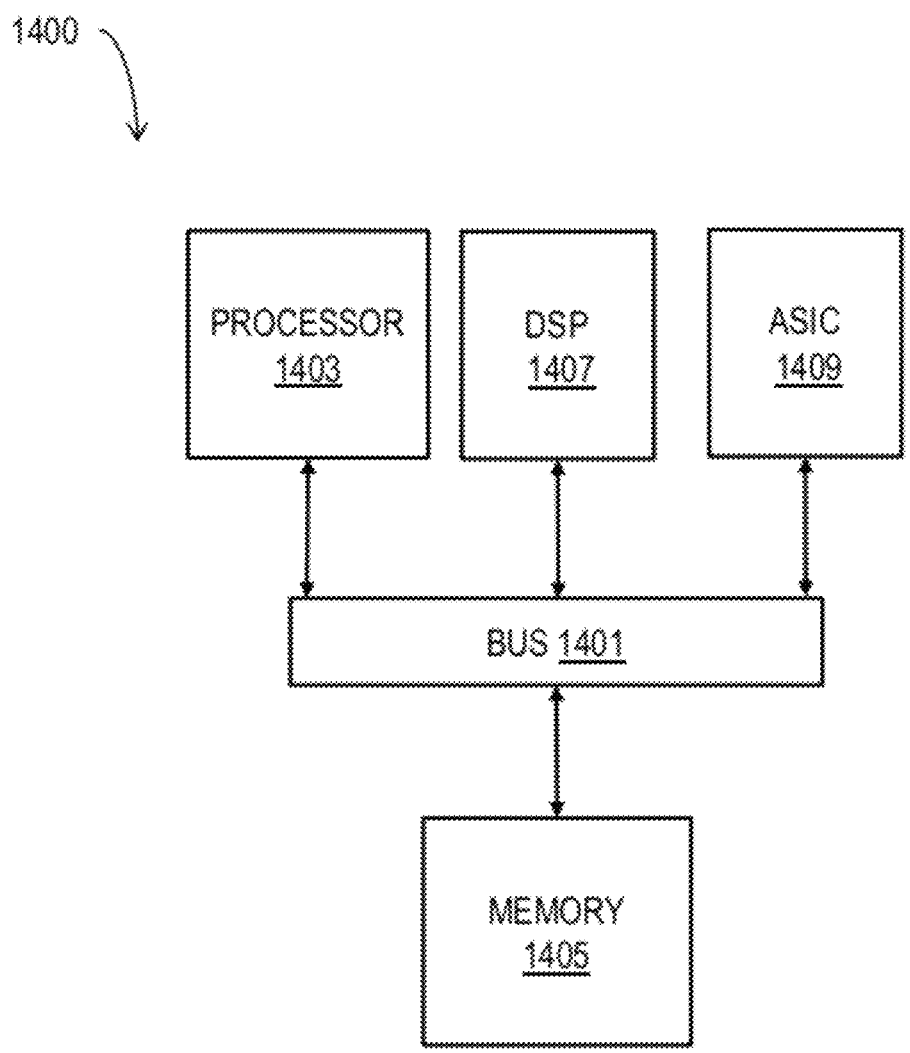
FIG. 14 illustrates a chip set upon which an embodiment of the invention may be implemented.

FIG. 14 illustrates a chip set 1400 upon which an embodiment of the invention may be implemented. Chip set 1400 is programmed to perform one or more steps of a method described herein and includes, for instance, the processor and memory components described with respect to FIG. 13 incorporated in one or more physical packages (e.g., chips). By way of example, a physical package includes an arrangement of one or more materials, components, and/or wires on a structural assembly (e.g., a baseboard) to provide one or more characteristics such as physical strength, conservation of size, and/or limitation of electrical interaction. It is contemplated that in certain embodiments the chip set can be implemented in a single chip. Chip set 1400, or a portion thereof, constitutes a means for performing one or more steps of a method described herein.

In one embodiment, the chip set 1400 includes a communication mechanism such as a bus 1401 for passing information among the components of the chip set 1400. A processor 1403 has connectivity to the bus 1401 to execute instructions and process information stored in, for example, a memory 1405. The processor 1403 may include one or more processing cores with each core configured to perform independently. A multi-core processor enables multiprocessing within a single physical package. Examples of a multi-core processor include two, four, eight, or greater numbers of processing cores. Alternatively or in addition, the processor 1403 may include one or more microprocessors configured in tandem via the bus 1401 to enable independent execution of instructions, pipelining, and multithreading. The processor 1403 may also be accompanied with one or more specialized components to perform certain processing functions and tasks such as one or more digital signal processors (DSP) 1407, or one or more application-specific integrated circuits (ASIC) 1409. A DSP 1407 typically is configured to process real-world signals (e.g., sound) in real time independently of the processor 1403. Similarly, an ASIC 1409 can be configured to performed specialized functions not easily performed by a general purposed processor. Other specialized components to aid in performing the inventive functions described herein include one or more field programmable gate arrays (FPGA) (not shown), one or more controllers (not shown), or one or more other special-purpose computer chips.

The processor 1403 and accompanying components have connectivity to the memory 1405 via the bus 1401. The memory 1405 includes both dynamic memory (e.g., RAM, magnetic disk, writable optical disk, etc.) and static memory (e.g., ROM, CD-ROM, etc.) for storing executable instructions that when executed perform one or more steps of a method described herein. The memory 1405 also stores the data associated with or generated by the execution of one or more steps of the methods described herein.

4. Alternatives and Modifications

In the foregoing specification, the invention has been described with reference to specific embodiments thereof. It will, however, be evident that various modifications and changes may be made thereto without departing from the broader spirit and scope of the invention. The specification and drawings are, accordingly, to be regarded in an illustrative rather than a restrictive sense.

What is claimed is:

1. A method comprising:
   Receiving on a processor data that indicates a sequence of nucleotides on at least a first strand of a nucleic acid;
   determining on a processor values for a plurality of physical properties for each portion of the at least first strand; and
   determining, on a processor, based at least in part on a finite element numerical model and the plurality of physical properties for each portion, a value of at least one derived structural property of a nanostructure that comprises the at least first strand of nucleic acid.

2. A method as recited in claim 1, wherein the plurality of physical properties for each portion is selected from a group containing length of the portion, stretching spring constant of the portion, bending spring constant of the portion, twisting spring constant of the portion, electrostatic charge of the portion, steric repulsion of the portion, salvation energy of the portion, and rupture criteria for the portion.

3. A method as recited in claim 1, determining values for the plurality of physical properties for each portion of the at least first strand further comprises storing values for the plurality of physical properties in a finite element data item for the finite element model.

4. A method as recited in claim 1, wherein the at least one derived property is selected from a group containing relaxed shape, internal strain energy, normal modes of vibration, and stiffness.

5. A method as recited in claim 1, further comprising presenting the derived property of the nanostructure to a user.

6. A method comprising:
receiving on a processor data that indicates a sequence of nucleotides on at least a first strand of a nucleic acid;
determining on a processor values for at least one physical property for each portion of the at least first strand;
determining on a processor, based at least in part on a finite element numerical model and the physical properties for each portion, a value of at least one derived property of a nanostructure that comprises the at least first strand of nucleic acid;
determining a difference between the value of the at least one derived property of the nanostructure and a target value of the at least one derived property; and
if the difference does not exceed a predetermined threshold, then fabricating the nanostructure based on the sequence of nucleotides on at least the first strand of the nucleic acid.

7. A method as recited in claim 6, further comprising, if the difference exceeds the predetermined threshold, then:
determining on a processor a change in the sequence of nucleotides on at least the first strand based on the difference;
determining on a processor, based at least in part on the numerical model and the physical properties for each portion, a revised value of at least one derived property of a revised nanostructure that comprises the change in the sequence of nucleotides;
determining on a processor a revised difference between the value of the at least one derived property of the nanostructure and the target value; and
if the revised difference does not exceed the predetermined threshold, then fabricating the nanostructure based on the change in the sequence of nucleotides on at least the first strand.

8. A method as recited in claim 1, further comprising:
fabricating the nanostructure based on the sequence of nucleotides on at least the first strand of the nucleic acid;
determining a measured value of the at least one derived property of the fabricated nanostructure based on a measurement of the fabricated nanostructure;
determining a difference between the value of the at least one derived property of the nanostructure and the measured value; and
determining a change for at least one value for the at least one physical property for at least one portion of the first strand based on the difference.

9. A method as recited in claim 1, wherein:
the nucleic acid is deoxyribonucleic acid; and
receiving data that indicates the sequence of nucleotides on at least the first strand of the nucleic acid further comprises receiving data that indicates a sequence of nucleotides on each of a plurality of short strands of deoxyribonucleic acid, wherein each short strand is complimentary to a unique portion of the first strand; and
determining the value of the at least one derived property of the nanostructure that comprises the first strand of nucleic acid further comprises determining a value of at least one derived property of a nanostructure that comprises a hybridized binding of the first strand to the plurality of short strands.

10. A method as recited in claim 9, wherein at least one short strand is complimentary to a unique non-contiguous set of segments of the first strand.

11. A method as recited in claim 1, wherein each portion shares the same value for the plurality of physical properties.

12. A method as recited in claim 1, wherein determining values for at least one physical property for each portion of the at least first strand further comprises:
determining a first value for the at least one physical property for a portion comprising a hybridized base pair; and
determining a different second value for the at least one physical property for a portion comprising a Holliday junction.

13. A method comprising:
receiving on a processor data that indicates a sequence of nucleotides on at least a first strand of a nucleic acid;
determining on a processor values for at least one physical property for each portion of the at least first strand; and
determining on a processor, based at least in part on a finite element numerical model and the physical properties for each portion, a value of at least one derived property of a nanostructure that comprises the at least first strand of nucleic acid, further comprising:
determining whether adjacent double strands of a nucleic acid have a same number of nucleotide base pairs between adjacent Holliday junctions; and
if so, then determining a net twist introduced between the adjacent Holliday junctions.

14. A method as recited in claim 13, wherein determining the value of the derived property of the nanostructure further comprises, if the adjacent double strands of a nucleic acid have a different number of nucleotide base pairs between adjacent Holliday junction, then determining a net bend and net twist introduced between the adjacent Holliday junctions.

15. A method as recited in claim 14, wherein determining the net bend and net twist introduced between the adjacent Holliday junctions further comprises:
applying a reference force comprising a reference stretching force to avoid a bend or a reference torque to align base pairs or both; and
subsequently relaxing the reference force incrementally.

16. An apparatus comprising:
a processor; and
a computer-readable medium,
wherein the computer-readable medium carries one or more sequences of instructions, wherein execution of the one or more sequences of instructions by the processor causes the apparatus at least to
receive data that indicates a sequence of nucleotides on at least a first strand of a nucleic acid;
determine values for a plurality of physical properties for each portion of the at least first strand; and
determine, based at least in part on a finite element numerical model and the physical properties for each portion, a value of at least one derived structural property of a nanostructure that comprises the at least first strand of nucleic acid.

17. A non-transitory computer-readable storage medium carrying one or more sequences of instructions, wherein execution of the one or more sequences of instructions by one or more processors causes an apparatus to:
- receive data that indicates a sequence of nucleotides on at least a first strand of a nucleic acid;
- determine values for a plurality of physical properties for each portion of the at least first strand; and
- determine, based at least in part on a finite element numerical model and the physical properties for each portion, a value of at least one derived structural property of a nanostructure that comprises the at least first strand of nucleic acid.

18. A method as recited in claim 6, further comprising:
- determining a measured value of the at least one derived property of the fabricated nanostructure based on a measurement of the fabricated nanostructure;
- determining a second difference between the value of the at least one derived property of the nanostructure and the measured value; and
- determining a change for at least one value for the at least one physical property for at least one portion of the first strand based on the second difference.

* * * * *